(12) United States Patent
Bandodkar et al.

(10) Patent No.: US 9,340,496 B2
(45) Date of Patent: May 17, 2016

(54) PROCESS FOR THE PRODUCTION OF A SULFONE MONOMER

(76) Inventors: Hemant Ratanakar Bandodkar, Thane West (IN); Dilip Chandrakant Sawant, Dombivli East (IN)

( * ) Notice: Subject to any disclaimer, the term of this patent is extended or adjusted under 35 U.S.C. 154(b) by 223 days.

(21) Appl. No.: 13/513,399

(22) PCT Filed: Nov. 30, 2010

(86) PCT No.: PCT/IB2010/003057
§ 371 (c)(1),
(2), (4) Date: Jun. 1, 2012

(87) PCT Pub. No.: WO2011/067649
PCT Pub. Date: Jun. 9, 2011

(65) Prior Publication Data
US 2012/0302795 A1 Nov. 29, 2012

(30) Foreign Application Priority Data
Dec. 1, 2009 (GB) .................................. 0921069.1

(51) Int. Cl.
*C07C 315/00* (2006.01)
*C07C 317/06* (2006.01)

(52) U.S. Cl.
CPC ............. *C07C 315/00* (2013.01); *C07C 317/06* (2013.01)

(58) Field of Classification Search
None
See application file for complete search history.

(56) References Cited

U.S. PATENT DOCUMENTS

| 2,288,282 A | 6/1942 | Huismann |
| 3,334,146 A | 8/1967 | Pitt et al. |
| 4,012,451 A | 3/1977 | Enoki et al. |
| 5,082,973 A | 1/1992 | Stumpp et al. |

OTHER PUBLICATIONS

Davies et al., "A supramolecular carpet formed via self-assembly of bis(4,4'-dihydroxyphenyl) sulphone," Journal of the Chemical Society, Chemical Communications (1997) 567-568.

*Primary Examiner* — Clinton Brooks
(74) *Attorney, Agent, or Firm* — Volpe and Koenig, P.C.

(57) ABSTRACT

The present invention provides a method for the preparation of polymer grade 4,4'-dichlorodiphenyl sulfone in steps comprising reacting dimethyl sulfate and sulfur trioxide optionally containing a catalyst; reacting the formed dimethyl pyrosulfate with the unreacted sulfur trioxide optionally in the presence of a catalyst; reacting the reaction mixture with monochlorobenzene optionally containing a catalyst; optionally removing unreacted dimethyl sulfate; isolating crude 4,4'-dichlorodiphenyl sulfone using an organic solvent/organic solvent-water mixture; recovering the solvent from mother liquor; optionally recovering the isomeric mixture of dichlorodiphenyl sulfones from mother liquor; optionally, conversion of residual isomeric mixture of dichlorodiphenyl sulfones to a product selected from diphenyl sulfone, 2-aminodiphenyl sulfone; 2,4'-dihydroxydiphenyl sulfone, 4,4'-dihydroxydiphenyl sulfone; optionally recovering monochlorobenzene sulfonic acid and/or monochlorobenzene from the mother liquor; optionally recovering sulfuric acid from the residual liquor; optionally recycling the solvent; and purifying 4,4'-dichlorodiphenyl sulfone from crude followed by crystallization. Further the present invention discloses a process in which isomeric mixture of 4,4'-, 3,4'-, and 2,4'-dichlorodiphenyl sulfone produced during the preparation of 4,4'-dichlorodiphenyl sulfone is converted to value added products such as diphenyl sulfone, 2,4'-dihydroxydiphenyl sulfone, 4,4'-dihydroxydiphenyl sulfone and 2-aminodiphenyl sulfone.

36 Claims, No Drawings

PROCESS FOR THE PRODUCTION OF A SULFONE MONOMER

This application is a 35 U.S.C. §371 national phase application of PCT/IB2010/003057, which was filed Nov. 30, 2010 and is incorporated herein by reference as if fully set forth.

The invention relates to an economical and environmentally friendly process for the production of substantially pure 4,4'-dichlorodiphenyl sulfone of polymer grade material in high yields.

4,4'-dichlorodiphenyl sulfone (DCDPS) is important as a starting material of polysulfones and polyethersulfones. Polysulfones and ployethersulfones are a family of thermoplastics known as engineering plastics and are used in high temperature applications. Polysulfones are used in the manufacture of medical equipment (nebulizers and dialysis components), appliances (Coffee makers, humidifiers and microwave ovens), automobile parts (steering column lock switches, relay insulators and pistons), and electrical equipment (television components and capacitor film). DCDPS has also been show to be as a potent insecticide as dichlorodiphenyl trichloroethane (DDT) for the Musca nebulo. DCDPS has also been used as pesticide and in reactive dyes in the textile industry. For such applications, 4,4'-dichlorodiphenyl sulfone that is substantially free of 2,4' and 3,4' dichlorodiphenyl sulfone is required.

DE-A 1087592 or U.S. Pat. No. 2,971,985 discloses a process for the preparation of 4,4'-dichlorodiphenyl sulfone in which stabilized sulfuric anhydride under the trade name "Sulfan" is reacted with dimethyl sulfate wherein two moles of "Sulfan" is reacted with one mole of dimethyl sulfate at <100° C., to give a solution containing one mole of sulfuric anhydride and one mole dimethyl pyrosulfate which is then reacted with two moles of chlorobenzene at 50° C. to 55° C., then adding water to precipitate 4,4'-dichlorodiphenyl sulfone in 90% yield. This scheme suffers from the shortcoming that one of the byproduct 4-chlorobenzenesulofonic acid is toxic. Further the purity of the end product is not suitable for polymer synthesis.

JP 09157246 discloses a process for isolating 4,4'-dichlorodiphenyl sulfone by crystallization by dissolving a mixture of 4,4'-dichlorodiphenyl sulfone and sulfuric acid in organic solvent and water. Organic solvent is selected from benzene, toluene, xylene, fluorobenzene, chlorobenzene, o-dichlorobenzene, bromobenzene, dichloromethane, chloroform, 1,2-dichloroethane, 1,2-dichloropropane. The yield of dichlorodiphenyl sulfone is only 73.3% on basis of chlorobenzene used and purity of 4,4'-dichlorodiphenyl sulfone is 99.88%. Further the formation of 4-chlorobenzenesulfonic acid as a byproduct is toxic.

JP 09188663 A discloses a process for the preparation of 4,4'-dichlorodiphenyl sulfone in which dimethyl sulfate containing oxo boron compound is reacted with sulfur trioxide gaseous or liquid or commercially stabilized or stabilized by mixture of boron trioxide and dimethyl sulfate. The reaction mixture is further reacted with monochlorobenzene at 50-55° C. and after completion of the reaction; dimethyl sulfate is recovered to give a product with 99.5% with respect to of chlorobenzene and with selectivity of 4.3% chlorobenzene sulfonic acid and 95.5% dichlorodiphenyl sulfone. The reaction mixture is treating with water to obtain dichlorodiphenyl sulfone 95.0% yield based on chlorobenzene. This scheme suffers from the shortcoming that one of the byproducts, 4-chlorobenzenesulofonic acid, is toxic. The patent does not disclose the selectivity of 4,4'-dichlorodiphenyl sulfone and its isomers.

DE-A No. 2704972 or U.S. Pat. No. 4,172,852, describes a method for the preparation of 4,4'-dichlorodiphenyl sulfone in which Friedel-Crafts reaction of 4-chlorbenzenesulfonyl chloride with monochlorobenzene in present of catalyst such as Iron(II) chloride is carried out. This process has the disadvantage that Iron(II) chloride acts as a chlorinating agent for monochlorobenzene at 140° C. thereby forming substantial amounts of dichlorobenzene as byproduct. This requires extensive working up.

GB Patent Application 2135666A describes a process for the preparation of 4-chlorobenzenesulfonyl chloride by reacting chlorobenzene with chlorosulfonic acid in halogenated aliphatic hydrocarbons in the presence of alkali metal salt of mineral acid and/or ammonium salt of a mineral acid. The 4-chlorobenzenesulfonyl chloride obtained is converted into 4,4'-dichlorodiphenyl sulfone by reacting it with chlorobenzene in the presence of a catalytic amount of ferric chloride at 145° C. to 155° C. for considerable time. The best results reported were 93.8% yield with purity of 89.8% of 4,4'-dichlorodiphenyl sulfone. This product is also not suitable for polymer based applications.

DE-A No. 2252571 or U.S. Pat. No. 3,855,312, describes the synthesis of 4,4'-dichlorodiphenyl sulfone from monochlorobenzene and 4-chlorobenzenesulfonic acid under elevated pressure and temperatures of from 220 to 260° C. with long reaction times of about 16 hours which is not desirable as they produce low yield (80%) and low selectivity (88%).

U.S. Pat. No. 4,983,773 or JP 02169565 discloses a reaction in which a condensing agent such as boric acid (5 to 10 mole % on 1 mole sulfuric acid) and trifluoromethanesulfonic acid (0.05 to 0.5 mole % on 1 mole of sulfuric acid) is added during the preparation of 4,4'-dichlorodiphenyl sulfone by heating a mixture of chlorobenzene and sulfuric acid to 200° C. to 250° C. maintaining pressure of 4 to 5 bar. The reaction is generally completed in 10 hours and water is removed by azeotropic distillation.

U.S. Pat. No. 5,082,973 or JP 02235856 discloses a continuous process in which sulfur trioxide, dimethyl sulfate and chlorobenzene are reacted at 50 to 100° C. in tubular reactor with packing elements made of sintered boric acid balls or silica gel elements doped with an acid such as phosphoric, sulfuric or boric acid. The boric acid balls are generally sintered at a temperature of from 150 to 200° C.

Chemical Abstract No. 114:150123y and CN 1623982A, documents a process for preparation of 4,4'-dichlorodiphenyl sulfone by Ma Bingrong (CN) in which 25% to 90% $SO_3$ is dissolved in couplant (di-Me sulfate; di-Me carbonate; Me nitrate; tri-Bu phosphate) at 0 to 120° C.; adding 0.01 to 10% catalyst in the $SO_3$ solution at 15° C. to 150° C. to give functional solution which is then reacted with chlorobenzene at 15° C. to 160° C. for 5 to 600 mins and cool to 10° C. to −15° C. to give product in low yield (70% to 72%) and low selectivity (melting point 147.6° C. to 147.8° C.). The catalyst can be active carbon, alumina, boron oxides or active floridin.

Chemical Abstract No. 134:131313n, describes the preparation of 4,4'-dichlorodiphenyl sulfone by sulfonation of chlorobenzene with gaseous sulfur trioxide and dimethyl sulfate contg. 1 to 10% boron trifluoride etherate or 1 to 10% tri-Me borate followed by water to precipitate the product followed by recyrstallisation.

U.S. Pat. No. 3,309,409 discloses a process for the separation of 4,4'-dichlorodiphenyl sulfone from a reaction mixture wherein the reaction mixture is added to water or aqueous alkali to precipitate the product. However the precipitated product gets contaminated with chlorobenzenesulfonic acid, methyl sulfonic acid, the isomers of 2,4' and 3,4' and other impurities.

U.S. Pat. No. 3,415,887 discloses a process for the separation of 4,4'-dichlorodiphenyl sulfone by dissolving the reaction mixture in methylene chloride, neutralizing the acidic materials by aqueous alkali, evaporating the separated methylene chloride solution to dryness. The end product is generally contaminated with the isomers 2,4' and 3,4' due to their high solubility in methylene chloride.

U.S. Pat. No. 3,355,497 describes a process in which a mixture of one mole of dimethyl pyrosulfate and 2 to 3 moles of sulfur trioxide is reacted with chlorobenzene. In this method excess sulfur trioxide is used negatively impacting the economics and industrial applicability of the process.

U.S. Pat. No. 1,570,046 describes a process of sulfonating beta naphthol. In this process catalytic amount of boric acid improves the yield and the quality of the mixed sulfonic acid.

U.S. Pat. No. 3,334,146 describes a process in which the reaction mixture is dissolved in monochlorobenzene and the solution is washed with water. The washed solution is cooled to precipitate 4,4'-dichlorodiphenyl sulfone. Though this process yields considerably pure product the yield achieved are as low as 75% to 80% and the recovery of the product from the mother liquor involves extensive working.

U.S. Pat. No. 4,012,451, describes a process for the separating highly pure 4,4'-dichlorodiphenyl sulfone from the reaction mixture which contains 2,4' and 3,4'-isomers which comprises dissolving the reaction mixture in an organic solvent selected from the group consisting of trichloroethylene, tetrachloroethylene and mixture thereof and cooling the organic solution to precipitate 4,4'-dichlorodiphenyl sulfone. Even though considerably pure product is obtained, the process involves complex multiple recovery stage working.

U.S. Pat. No. 4,873,372 and EP 0279387, describe a process for the isolation of 4,4'-dichlorodiphenyl sulfone largely free from other isomers. The mixture of dichlorodiphenyl sulfones is treated with an alkanol at 20° C. to 250° C. under substantially water free conditions in such a manner that dissolution in the alkanol is completed as much as possible, then cooling the resultant substantially water free mixture to precipitate pure 4,4'-dichlorodiphenyl sulfone. The examples given in the patent indicates that the treatment is carried out at 3.5 to 6 Bar. The drawback is that under such conditions olefin formation can take place.

EP Patent 0279388, describes a process for the preparation of 4,4'-dichlorodiphenyl sulfone by reacting of chlorobenzene with excess chlorosulfonic acid or sulfur trioxide and excess thionyl chloride or phosgene at about 220° C. The yields are approx 74% with purity of 99.6%. However the use of phosgene or thionyl chloride is undesirable in large scale operations.

DE 4001615 (A1) describes production of bis(4-chlorophenyl) sulphone by reacting chlorobenzene with bis(trimethylsilyl) pyrosulfate and sulfur trioxide at 20° C. to 100° C. Bis(trimethylsilyl) pyrosulfate is formed in situ from bis(trimethylsilyl) sulfate and sulfur trioxide.

DE 3902893 (A1) describes process for the preparation of bis(4-chlorophenyl) sulfone by reacting bismuth tri(4-chlorobenzenesulphinate) in the presence of oxygen at a room temperature of 200° C. to 250° C. and pressures of 0.1 to 500 bar.

Canadian Patent CA 846214, describes a process for the preparation of 4,4'-dichlorodiphenyl sulfone, which comprises reacting 1 mole of stabilized sulfur trioxide (Sulfan) and 3 moles of diethyl sulfate at below 10° C. to form a reaction mass containing unreacted diethyl sulfate and the reaction product of sulfur trioxide and diethyl sulfate. Thereafter reacting said reaction mass with about a 4 moles of chlorobenzene and 1 mole of sulfur trioxide at a temperature not greater than about 15° C. and recovering 4,4'-dichlorodiphenyl sulfone in yield of 77.5% of 98.9% selectivity. The drawback of the process is the excess use of diethyl sulfate thereby generating diethyl pyrosulfate which is a toxic byproduct.

There remains a need to provide a process which produces 4,4'-dichlorodiphenyl sulfone of a certain level of purity for use in polymer applications. Further, there is a need to reduce or avoid the production of toxic by-products and to provide a process which is economic and which minimizes the amount of work-up of the crude product.

The main object of the invention is to provide an economical and environmentally friendly method for the preparation of 4,4'-dichlorodiphenyl sulfone reducing or overcoming one or more and desirably all the shortcomings of the prior art.

Another object of the invention is to provide a process for the preparation of 4,4'-dichlorodiphenyl sulfone substantially free of 2,4' and 3,4'-isomers of dichlorodiphenyl sulfone.

Another object of the invention is to provide a process for the preparation of 4,4'-dichlorodiphenyl sulfone with yield of over 90%.

Another object of the invention is to provide a process for the preparation of 4,4'-dichlorodiphenyl sulfone of polymer grade material.

Another object of the invention is to provide a process for the preparation of 4,4'-dichlorodiphenyl sulfone with substantially reduced reaction times as compared to prior art reaction times.

Another object of the invention is to provide a process for the preparation of 4,4'-dichlorodiphenyl sulfone in which catalysts are used without the need to prepare catalyst impregnated sintered glass or silica balls.

Another object of the invention is to provide a process for the preparation of 4,4'-dichlorodiphenyl sulfone with enhanced color specifications.

Another object of the invention is to provide a process for the preparation of 4,4'-dichlorodiphenyl sulfone wherein no olefins are formed while recovering the alkanol such as Isopropanol.

Another object of the invention is to provide a process for the preparation of 4,4'-dichlorodiphenyl sulfone without the production of toxic byproducts such as dimethyl pyrosulfate and reducing the load on effluent treatment plants.

Another object of the invention is to provide a process for the preparation of 4,4'-dichlorodiphenyl sulfone in which the reactants and byproducts are substantially recycled.

The invention provides in a first aspect a process for the production of 4,4'-dichlorodiphenyl sulfone comprising contacting dimethyl sulfate with sulfur trioxide to provide a reaction mixture comprising dimethyl pyrosulfate and sulfur trioxide, contacting the reaction mixture with chlorobenzene to produce a crude 4,4'-dichlorodiphenyl sulfone product mix and isolating 4,4'-dichlorodiphenyl sulfone from the said product mix.

The invention is especially beneficial in producing 'Polymer grade' 4,4'-dichlorodiphenyl sulfone. Reference to "polymer grade" material in this document refers to an isomeric content of at least 99%, preferably 99.5% or more of 4,4'-dichlorodiphenyl sulfone in the product.

'Crude' 4,4'-dichlorodiphenyl Sulfone in this document refers to a product mix containing an isomeric content of the 4,4' isomer less than the polymer grade content of the 4,4' isomer. Suitably, the crude product mix comprises 4,4'-dichlorodiphenyl sulfone at a level of up to 99% for example from 30% to 99%.

Suitably, sulfur trioxide optionally containing a catalyst is reacted with dimethyl sulfate. Alternately, this catalyst could be present in dimethyl sulfate before it is contacted with Sulfur trioxide. As another alternative, this catalyst could be present in a mixture of dimethyl sulfate and sulfur trioxide. As another alternative, this catalyst could be added to monochlorobenzene before contacting it with the mixture of dimethyl sulfate and sulfur trioxide.

Preferably, the product mix is contacted with an organic solvent to isolate 4,4'-dichlorodiphenyl sulfone from the said product mix. Desirably, the isolated 4,4'-dichlorodiphenyl sulfone is then further purified.

In a preferred embodiment, the purification is carried out by contacting the crude 4,4'-dichlorodiphenyl sulfone product mix or isolated 4,4'-dichlorodiphenyl sulfone with a solvent comprising an organic component and an aqueous component, for example an aromatic hydrocarbon and water. Suitably the weight ratio of crude 4,4'-dichlorodiphenyl sulfone:organic component is from 1:0.1 to 10. Examples of preferred organic component include monochlorobenzene. Preferably a sequestering agent is employed to remove undesired reaction products, by-products or unreacted starting materials into the aqueous component and the aqueous component and organic component are suitably separated, the organic component containing 4,4'-dichlorodiphenyl sulfone. Removal of the organic component suitably provides 4,4'-dichlorodiphenyl sulfone at a high level of purity.

Preferably, in accordance with this invention 4,4'-dichlorodiphenyl sulfone is prepared in steps comprising:
1. Reacting dimethyl sulfate and sulfur trioxide optionally containing a catalyst;
2. Reacting the formed dimethyl pyrosulfate with the unreacted sulfur trioxide optionally in the presence of a catalyst;
3. Reacting the reaction mixture with monochlorobenzene optionally containing a catalyst
4. Optionally removing unreacted dimethyl sulfate;
5. Isolating crude 4,4'-dichlorodiphenyl sulfone using an organic solvent/organic solvent-water mixture;
6. Recovering the solvent from mother liquor;
7. Optionally recovering of the isomeric mixture of ☐dichlorodiphenyl sulfones from mother liquor
8. Optionally, conversion of residual isomeric mixture of dichlorodiphenyl sulfones to commercially viable products, for example diphenyl sulfone, 2,4'-dihydroxydiphenyl sulfone, 4,4'-dihydroxydiphenyl sulfone, 2-aminodiphenyl sulfone;
9. Optionally recovering monochlorobenzene sulfonic acid and/or monochlorobenzene from the mother liquor,
10. Optionally recovering sulfuric acid from the residual liquor of step 8;
11. Optionally recycling the solvent;
12. Purifying crude 4,4'-dichlorodiphenyl sulfone by crystallization;

Suitably, 4,4'-dichlorodiphenyl sulfone is prepared in high yields and enhanced selectivity by reacting a mixture of one mole dimethyl sulfate and two moles of sulfur trioxide optionally containing a catalyst and then reacting the formed dimethyl pyrosulfate and the unreacted sulfur trioxide optionally in the presence of a catalyst and further reacting it with two moles of monochlorobenzene optionally containing a catalyst. The method preferably comprises preparing a mixture of dimethyl pyrosulfate and sulfur trioxide by reacting one mole dimethyl sulfate and two moles of sulfur trioxide and then adding a catalyst to this mixture to carry out the reaction at 10° C. to 120° C. which is further reacted with monochlorobenzene at 10° C. to 120° C. for 30 to 300 min followed by treatment with an organic solvent or organic solvent-water mixture at 20° C. to 100° C., cooling, and separating the precipitate to achieve a yield of 80% of 99% purity 4,4'-dichlorodiphenyl sulfone. Desirably, the product is further purified using monochlorobenzene to obtain polymer grade material. The process of this invention provides options for recycling the solvents and converting the residual isomeric mixture of dichlorodiphenyl sulfone to commercially viable products such as diphenyl sulfone, 2-aminodiphenyl sulfone, 2,4'-dihydroxydiphenyl sulfone and 4,4'-dihydroxydiphenyl sulfone. A process according to which, the catalyst is added to a mixture of dimethyl pyrosulfate and the unreacted sulfur trioxide or is added to two mole equivalents of sulfur trioxide and the mixture is added to the one mole equivalents of dimethyl sulfate or one mole equivalent of dimethyl sulfate and two mole equivalent of sulfur trioxide are reacted without a catalyst and the catalyst is added to the two mole equivalents of monochlorobenzene or a mixture of two mole equivalent of sulfur trioxide and one mole dimethyl sulfate equivalent of is added to two moles monochlorobenzene and the catalyst is added to this mixture.

The mother liquor containing the alkanol, methyl sulfuric acid, chlorobenzenesulfonic acid and the mixture of 4,4'; 3,4' & 2,4' dichlorodiphenyl sulfones may be further treated for their recovery. The chlorobenzenesulfonic acid in the mother liquor is suitably hydrolyzed to chlorobenzene and recycled.

Preferably, the reaction of one mole of dimethyl sulfate and two moles of sulfur trioxide is carried out at 10° C. to 120° C., preferably at 10° C. to 90° C., most preferably at 20° C. to 80° C.

In an embodiment of step 1, the molar ratio of sulfur trioxide to dimethyl sulfate is 2 to 1. Sulfur trioxide is preferably added to dimethyl sulfate optionally containing a catalyst although as an alternative embodiment dimethyl sulfate may be added to sulfur trioxide, optionally containing a catalyst.

In another embodiment of step 1, two moles sulfur trioxide and one mole of dimethyl sulfate are simultaneously added to a reaction zone to form the reaction mixture.

Most preferably, the addition of catalyst in to the mixture of one mole of dimethyl sulfate and two moles of sulfur trioxide is carried out at 10° C. to 120° C., preferably at 10° C. to 90° C., most preferably at 20° C. to 80° C.

Preferably, the reaction of catalyst treated mixture of one mole of dimethyl sulfate and two moles of sulfur trioxide with monochlorobenzene is carried out at 10° C. to 120° C., preferably at 10° C. to 90° C., most preferably at 20° C. to 80° C.

Preferably, the catalyst is selected from boron based compounds such as boric acid, boron trioxide or esters of boron based compounds or aluminium trioxide, used in concentrations of 0.01% to 10 mole %, preferably from 0.1% to 5 mole % and most preferably from 0.2% to 2.5 mole % based on one mole sulfur trioxide.

In an embodiment of this process, catalyst is added to a mixture of dimethyl pyrosulfate and unreacted sulfur trioxide in step 2.

In an embodiment of this process, two moles sulfur trioxide containing the catalyst is added to one mole of dimethyl sulfate in step 1.

In another embodiment two moles sulfur trioxide is added to the mixture of catalyst and one mole of dimethyl sulfate in step 1.

In another embodiment one mole dimethyl sulfate containing the catalyst is added to the two moles of sulfur trioxide in step 1.

In another embodiment two moles sulfur trioxide and one mole dimethyl sulfate is mixed simultaneously and then catalyst is added in mixture thereof in step 1.

In yet another embodiment the catalyst is added in two moles of monochlorobenzene in step 3 and is not added in step 1 or 2.

In yet another embodiment a mixture of two moles of sulfur trioxide and one mole of dimethyl sulfate is added to two moles of monochlorobenzene and the catalyst is added to this mixture.

The preferred embodiment in step 2, is the addition of catalyst to a mixture of two moles of sulfur trioxide to one mole of dimethyl sulfate.

Optionally the unreacted dimethyl sulfate after reaction of dimethyl pyrosulfate and unreacted sulfur trioxide with monochlorobenzene is removed from the reaction mixture by vacuum distillation with a vacuum 0.1 to 5 mm·Hg at 120 to 190° C., preferably at 140° C. to 180° C.

The solvent is suitably selected from alkanol such as methanol, ethanol, isopropanol, isobutanol, alkanol-water mixture or halogenated aliphatic solvents such as dichloromethane, 1,2-dichloroethane. The preferred solvents include isopropanol, isobutanol and an alkanol-water mixture. In one of the embodiments water may be used as the solvent. The advantage of using the alkanol over the chlorobenzene for reaction of 4,4'-dichlorodiphenyl sulfone is given after Ex. No. 15.

The ratio of solvent to the reaction mixture on weight basis is suitably 1:0.2 to 1:2, preferably 1:0.4 to 1:0.6.

Preferably, the solvent-water mixtures used are selected from water mixture with isopropanol or isobutanol, preferably isopropanol-water mixture.

Preferably, the ratio of solvent-water mixture to the reaction mixture on weight basis is 1:0.2 to 1:2, preferably 1:0.4 to 1:0.6 with respect to solvent.

Preferably, the reaction mixture is treated with solvent or solvent-water mixture at 10° C. to 120° C., preferably at 20° C. to 85° and most preferably at 40° C. to 60° C.

Preferably, the slurry of solvent or solvent-water mixture and product is cooled to 10° C. to 50° C., preferably to 20° C. to 30° C.

Suitably, the purification of crude dichlorodiphenyl sulfone is carried out in steps of:
  a. Treating with water immiscible solvent-water mixture at 85° C. to 95° C.;
  b. Treating with sequestering agent and/or activated carbon at 85° C. to 95° C. in presence of water immiscible solvent or water immiscible solvent-water mixture;
  c. Washing the solvent layer with water at 85° C. to 95° C. to remove water soluble impurities;
  d. Filtering the solvent layer at 85° C. to 95° C. to remove water insoluble impurities;
  e. Cooling the solvent to crystallize the product and filtering the same to isolate the product.

Suitably, the crude dichlorodiphenyl sulfone contains at least 90% 4,4'-isomer. The solvent is preferably selected from monochlorobenzene, toluene, trichloroethylene and tetrachloroethylene.

The ratio of crude 4,4'-dichlorodiphenyl sulfone, with the water immiscible solvent-water mixture on weight basis is suitably 1:1 to 1:4, preferably 1:1.5 to 1:2.5.

The ratio of water immiscible solvent with water on weight basis is suitably 1:0.5 to 1:2, preferably 1:0.8 to 1:1.2.

Desirably, the sequestering agent is selected from phosphonic acid compounds used in concentrations of 0.025% to 5% w/w, preferably 0.1 to 1% w/w based on crude 4,4'-dichlorodiphenyl sulfone.

Suitably, activated carbon is used in concentrations of 0.025% to 5% w/w, preferably 0.1 to 1% w/w based on crude 4,4'-dichlorodiphenyl sulfone.

Preferably, the treated mixture is crystallized by cooling to a temperature of 10° C. to 40° C., preferably 20° C. to 30° C.

Optionally the solvent, isopropanol is recovered by azeotropic distillation with water by adding water externally in mother liquor in ratio 1:0.5 to 1:3.0, preferably 1:1 to 1:1.5 with reaction mixture at temperature 80° C. to 115° C.

Optionally, after removal of isopropanol from mother liquor, the precipitate of isomeric mixture of dichlorodiphenyl sulfone is washed with water and neutralized by aqueous caustic soda lye. The product composition by HPLC analysis is 25% to 35% of 4,4'-dichlorodiphenylsulfone, 5% to 10% of 3,4'-isomer and 50% to 70% of 2,4'-isomer.

Optionally, the residue containing the isomeric mixture of dichlorodiphenyl sulfones is converted to commercially viable derivatives by catalytic reduction. The reaction is carried out in an organic solvent in which the isomeric mixture is catalytically dechlorinated using hydrogen in presence of reducing catalyst and a dehydrohalogenating agent at 20° C. to 120° C. and pressures up to 6 Bar to obtain a mixture of diphenyl sulfone also containing monochlorodiphenyl sulfones. This mixture is treated with an oxidizing agent in halogenated hydrocarbons and recrystallized in halogenated hydrocarbons to obtain diphenyl sulfone of 99% purity. This process can be used for preparation of diphenyl sulfone from any isomeric mixture of 2,4'-, 3,4'- and 4,4'-dichlorodiphenyl sulfone. Optionally controlled catalytic dechlorination results in a mixture of diphenyl sulfone and monochlorodiphenyl sulfones which is further treated with liquor ammonia at 100-300° C. in presence of a catalyst to obtain a mixture of 2-aminodiphenyl sulfone and diphenyl sulfone. Suitably, this mixture is further treated with mixture of alkanol and acid and 2-amino diphenyl sulfone is isolated by repeated solvent extraction. This product is then purified in aqueous alkanol. Optionally monochlorodiphenyl sulfone obtained after removal of halogenated hydrocarbons collected in crystallization of diphenyl sulfone, is treated with liquor ammonia at 100-300° C. in presence of a catalyst to give 2-aminodiphenyl sulfone which is further purified with aqueous alkanol.

Optionally, the residue containing an isomeric mixture of dichlorodiphenyl sulfones is hydrolyzed at temperatures between 100 to 300° C. to obtain 4,4' and 2,4' dihydroxy diphenyl sulfone of >99% purity. The method comprising reaction of isomeric mixture of dichlorodiphenyl sulfones and aqueous solution of sodium hydroxide in weight ratio of 1:6.5 at 100° C. to 300° C. for 2 to 8 hours, followed by treatment with dilute sulfuric acid to obtain a mixture of 4,4' and 2,4'-dihydroxy diphenyl sulfone whose pH is adjusted to separate the two isomers which are then recrystallized in alkanol to produce 4,4'- and 2,4'-dihydroxydiphenyl sulfone of 99% purity. This process can be used for preparation of 4,4' and 2,4'-dihdroxydiphenyl sulfone from any isomeric mixture of 2,4'-, 3,4'- and 4,4'-dichlorodiphenyl sulfone.

Optionally monochlorobenzene is recovered from the mother liquor by the hydrolysis of the by-product monochlorobenzene sulfonic acid at 170° C. to 250° C.

Optionally monochlorobenzene sulfonic acid is recovered from the mother liquor of step 6 or 7 and re-crystallized in concentrated sulfuric acid repeatedly to obtain >99% purity. The resultant high purity of monochlorobenzene sulfonic acid is then treated with a nitrating mixture of (nitric+sulfuric acid) to give o-nitro p-chlorobenzene sulfonic acid (ON-CBSA), which can be further purified through repeated crystallization.

Optionally sulfuric acid may be recovered from the residual liquor after recovery of monochlorobenzene. This residual liquor obtained from the recovery of monochlorobenzene contains traces of monochlorobenzene sulfonic acid in dilute sulfuric acid. The liquor is concentrated to 90% to 95% sulfuric acid by vacuum (0.1 to 5 mm·Hg) distillation at 150° C. to 180° C. followed by treatment with 50% hydrogen peroxide at 130° C. to 150° C. to get 80% to 90% of commercial grade sulfuric acid.

Optionally, the solvent may be recycled. The procedure followed is the same as that described above, except that the solvent is replaced by solvent-water mixture in ratio of 100:0.1 to 70:30 on weight basis.

When the solvent is an alkanol, the alkanol is recovered from alkanol-water mixture by distillation with starting mixtures of water to alkanol preferably of ratio 1:0.5 to 1:3.0, preferably 1:1 to 1:1.5 on weight basis.

Optionally, the solvent, isopropanol is recovered from isopropanol-water mixture by azeotropic distillation with water to maintain a ratio of 1:0.5 to 1:3.0, Preferably 1:1 to 1:1.5 on weight basis with reaction mixture at temperature 80° C. to 115° C.

In another embodiment, steps 1, 2 and 3 set out above is followed heating the reaction mixture at 120° C. to 190° C. in 0.1 to 0.5 mm Hg vacuum to recover the unreacted dimethyl sulfate.

In another embodiment, steps 1, 2 and 3 set out above is followed by isolation of the crude 4,4'-dichlorodiphenyl sulfone using an organic solvent/alkanol-water mixture.

In another embodiment, steps 1, 2, 3 and 5, set out above is followed by purification of the crude 4,4'-dichlorodiphenyl sulfone by treating with a mixture of water and water immiscible solvent in presence of sequestering agent, followed by crystallization.

In another embodiment, steps 1, 2, 3 and 5 set out above is followed by addition of water to the mother liquor of step 5 in weight ratio of 1:0.5 to 1:3.0 followed by distillation to recover the solvent and separating the isomeric mixture of dichlorodiphenyl sulfones.

In another embodiment, steps 1, 2, 3, 5, 6 and 7 set out above is followed by recovery of monochlorobenzene by hydrolyzing the residual mother liquor and distilling the monochlorobenzene.

In another embodiment of this process step (1, 2, 3, 5, 6 and 7) set out above involves the optional conversion of the effluent stream of monochlorobenzene sulfonic acid to a downstream value added product such as o-nitro, p-chlorobenzenesulfonic acid. The monochlorobenzene sulfonic acid isolated after the removal of solvent (alkanol) is then re-crystallized in concentrated sulfuric acid repeatedly to obtain >99% purity. The resultant high purity of monochlorobenzene sulfonic acid is then treated with a nitrating mixture of (nitric+sulfuric acid) to give the desired product which can be further purified through repeated crystallization.

In another embodiment of this process, steps 1, 2, 3, 5, 6, 7 and 9 set out above is followed by the removal of sulfuric acid by concentrating the residual mother liquor and treating with oxidizing agent to obtain 80% to 90% commercial grade sulfuric acid.

The process of the present invention provides in a preferred embodiment one or more, in combination of the following features:

addition of catalyst to the mixture of one mole of dimethyl sulfate and two moles of sulfur trioxide;

Reacting dimethyl sulfate and sulfur trioxide at 28 to 30° C.;

Addition of catalyst to the mixture of one mole of dimethyl sulfate and two moles of sulfur trioxide at 28 to 30° C.;

Reacting the formed dimethyl pyrosulfate with the unreacted sulfur trioxide in the presence of a catalyst at 28 to 30° C.;

Reacting the reaction mixture with monochlorobenzene at 30 to 35° C.;

Isolating crude 4,4'-dichlorodiphenyl sulfone using an organic solvent/organic solvent-water mixture;

recovering the solvent from mother liquor by distillation in the presence of water to reduce solvent losses due to degradation;

recovering the dichlorodiphenyl sulfones from mother liquor;

Conversion of residual Isomeric mixture of dichlorodiphenyl sulfones to commercially viable products such as diphenyl sulfone, 2-amino diphenyl sulfone, 2,4' dihydroxy diphenyl sulfone and 4,4' dihydroxy diphenyl sulfone;

recovering monochlorobenzene sulfonic acid and/or monochlorobenzene from the mother liquor;

recovering sulfuric acid from the residual liquor obtained after recovery of monochlorobenzene and/or monochlorobenzene;

recycling of recovered solvent.

In other embodiments a steps 1, 2, 3, 5 and 6, set out above is followed by converting the isomeric mixture of dichlorodiphenyl sulfones to commercially viable derivatives wherein:

(A). The reaction is carried out in an organic solvent in which the isomeric mixture is catalytically dechlorinated using hydrogen in presence of reducing catalyst and a dehydrohalogenating agent at 20° C. to 120° C. and pressures up to 6 Bar to obtain a diphenyl sulfone containing monochloro diphenyl sulfones. This mixture is treated with an oxidizing agent and recrystallized in halogenated hydrocarbons to obtain diphenyl sulfone of 99% purity. Optionally controlled catalytic dechlorination results in a mixture of diphenyl sulfone and monochlorodiphenyl sulfones which is further treated with liquor ammonia at 100-300° C. in presence of a catalyst to obtain a mixture of 2-aminodiphenyl sulfone & diphenyl sulfone. Suitably, this mixture is further treated with mixture of alkanol and acid and 2-amino diphenyl sulfone is isolated by repeated solvent extraction. This product is then purified in aqueous alkanol. Optionally monochlorodiphenyl sulfone obtained after removal of halogenated hydrocarbons collected in crystallization of diphenyl sulfone, is treated with liquor ammonia at 100-300° C. in presence of a catalyst to give 2-aminodiphenyl sulfone which is further purified with aqueous alkanol.

Or (B). Hydrolyzing the isomeric mixture of dichlorodiphenyl sulfones at temperatures between 100° C. to 300° C. to obtain 4,4' and 2,4'-dihydroxydiphenyl sulfone of >99% purity; The method comprising reaction of isomeric mixture of dichlorodiphenyl sulfone and aqueous solution of sodium hydroxide in weight ratio of 1:6.5 at 100° C. to 300° C. for 2 to 8 hours, followed by treatment with dilute sulfuric acid to obtain a mixture of 4,4' and 2,4'-dihydroxydiphenyl sulfone which is further pH adjusted to separate the two isomers which are then recrystallized in alkanol to produce 4,4' and 2,4'-dihdroxydiphenyl sulfone of 99% purity.

Thus, in accordance with the embodiment (A) indicated above, diphenyl sulfone and 2-aminodiphenyl sulfone is prepared from isomeric mixture of dichlorodiphenyl sulfone in steps comprising:
  a. Dissolving isomeric mixture of dichlorodiphenyl sulfones in organic solvent optionally in the presence of activated carbon at 80 to 100° C.;
  b. Dehalogenating dichlorodiphenyl sulfone in the presence of a catalyst;
  c. Removing catalyst and solvent from the reaction mixture to obtain a residue containing a mixture of diphenyl sulfone and monochlorodiphenyl sulfones;
  d. Dissolving the residue of step (c) in halogenated hydrocarbon and treating with oxidizing agent at 80-90° C., cooling to crystallize the diphenyl sulfone, separating the mother liquor and dissolving the diphenyl sulfone in halogenated hydrocarbon followed by carbon treatment at 80-90° C. and cooling to obtain diphenyl sulfone of at least 90% purity;
  e. Distilling the mother liquor of step (d) to isolate the residue containing monochloro diphenyl sulfones and diphenyl sulfones;
  f. Optionally treating the residue of step (c) with liquor ammonia to give a mixture of diphenyl sulfone and 2-aminodiphenyl sulfone followed by acid treatment with alkanol and repeated extraction with halogenated solvent to obtain 2-aminodiphenyl sulfone which is further purified with aqueous alkanol;
  g. Optionally treating the residue of monochlorodiphenyl sulfone obtained in step (e) with liquor ammonia to give a 2-aminodiphenyl sulfone which is further purified with aqueous alkanol.

The solvent is selected from alkanols such as methanol, ethanol, isopropanol, isobutanol; ethers such as 1,4-dioxane, methylcellosolve, ethylcellosolve preferably methylcellosolve. halogenated hydrocarbons such as dichloromethane, 1,2-dichloroethane; aromatic hydrocarbons such as benzene, toluene, xylene.

The ratio of solvent to reaction mixture on weight basis is 1:1-1:10, preferably 1:2-1:6.

The isomeric mixture of dichlorodiphenyl sulfone is optionally treated with activated carbon at 80-100° C.

The dehalogenating reaction of isomeric mixture of dichlorodiphenyl sulfone is carried out in hydrogen in the presence of a reduction catalyst and dehydrohalogenating agent in a temperature range of 20-200° C., preferably 20-120° C. and at atmospheric pressure to 50 Bar, preferably atmospheric pressure to 15 Bar.

The reduction catalyst is selected from metal catalysts such as Raney Nickel, Palladium on carbon or Platinum on carbon.

The reduction catalyst used is 1 to 40% by weight on the basis of dichlorodiphenyl sulfone, preferably at 10 to 30%.

The dehydrohalogenating agent is selected from oxides, hydroxides, carbonates or bicarbonates of alkaline or alkaline earth metals, ammonia and organic amines. However sodium hydroxide, potassium hydroxide, magnesium oxide, ammonium bicarbonate, potassium carbonate, ammonia, triethyl amine, triethanol amine are preferred.

The ratio of dehydrohalogenating agent to the dichlorodiphenyl sulfone is in the range of 1:0.1-1:5 by weight, preferably is 1:0.5-1:3.

The solvent used for purification is selected from halogenated hydrocarbons like dichloromethane, 1,2-dichloroethane, aromatic halogens, such as chlorobenzene, trichloroethylene and tetrachloroethylene. The preferred solvents are 1,2-dichloroethane, and chlorobenzene.

The ratio of solvent to the mixture of diphenyl sulfone and monochlorodiphenyl sulfone is 1:1-1:10 by weight; preferably 1:2-1:5.

The oxidizing agent is selected from peroxides such as hydrogen peroxide, chlorates, peroxydisulfates or a mixture thereof.

The solvent used for separation and recrystallization of diphenyl sulfone is selected from halogenated hydrocarbons like dichloromethane, 1,2-dichloroethane, aromatic halogens, such as chlorobenzene, trichloroethylene and tetrachloroethylene. The preferred solvents are 1,2-dichloroethane, and chlorobenzene.

The mixture of diphenyl sulfone and monochlorodiphenyl sulfones is ammonolysed with liquor ammonia at 100-300° C., preferably 200-250° in presence of a catalyst.

A 2-chlorodiphenyl sulfone is ammonolysed with liquor ammonia at 100-300° C., preferably 200-250° in presence of a catalyst.

The ratio of mixture of diphenyl sulfone and monochlorodiphenyl sulfone to ammonia on weight basis is 1:1-1:10, preferably 1:2-1:5.

The ratio of 2-chlorodiphenyl sulfone to ammonia on weight basis is 1:1-1:10, preferably 1:2-1:5.

A Catalyst is selected from metal chlorides or metal sulfates like copper chloride, cuprous chloride, and copper sulfate and its ratio with the mixture of diphenyl sulfone and monochlorodiphenyl sulfones on weight basis is 1-20%, preferably 1-10%.

Solvent selected for purification of 2-aminodiphenyl sulfone is selected from alkanol such as methanol, ethanol, isopropanol, alkanol-water mixture or halogenated aliphatic solvents such as dichloromethane, 1,2-dichloroethane or halogenated aromatic solvents like chlorobenzene, o-dichlorobenzene.

In accordance with the embodiment (B) indicated above, 4,4'- and 2,4'-dihydroxydiphenyl sulfone is prepared in steps comprising:
  i. Reacting isomeric mixture of dichlorodiphenyl sulfone with an aqueous solution of alkali in optionally aqueous or organic solvent or in mixture thereof;
  ii. Separating the unreacted dichlorodiphenyl sulfone by filtration;
  iii. Isolating crude mixture of 2,4'-dihydroxydiphenyl and 4,4'-dihydroxydiphenyl by precipitating with sulfuric or hydrochloric acid;
  iv. Dissolving the precipitating mixture in aqueous solution of sodium hydroxide;
  v. Separating of 4,4'-dihydroxydiphenysulfone, in form of monoalkali metal salt by adjusting the pH to 10.5-11.0 with sulfuric or hydrochloric acid;
  vi. Separating 2,4'-dihydroxydiphenyl sulfone from mother liquor of step (v), by adjusting pH to 5.0-5.5 with sulfuric or hydrochloric acid;
  vii. Purifying crude 2,4'-dihydroxydiphenyl sulfone by crystallization in aqueous alkanol;
  viii. Purifying crude 4,4'-dihydroxydiphenyl sulfone by crystallization in aqueous alkanol.

The reaction is carried out at 100° C. to 300° C., preferably 180 to 250° C., more preferably 200 to 240° C.

In step (i), the alkali is selected from sodium hydroxide, potassium hydroxide, lithium hydroxide preferably sodium hydroxide.

The weight ratio of alkali to dichlorodiphenyl sulfone being 1:2-1:10, preferably 1:3-1:8.

The weight ratio of dichlorodiphenyl sulfone to water as solvent being 1:2-1:10, preferably 1:2-1:5.

When organic solvent is used, the weight ratio of dichlorodiphenyl sulfone to organic solvent being 1:2-1:10, preferably 1:2-1:5.

When mixture of organic solvent-water is used, the ratio of dichlorodiphenyl sulfone to organic solvent-water mixture is between 1:2 and 1:10 preferably between 1:2 and 1:5 by weight.

The composition of the organic solvent:water mixture 1:1-1:6 by weight, preferably 1:2-1:5.

The solvent is selected from alkanol such as methanol, ethanol, isopropanol, alkanol-water mixture or halogenated aliphatic solvents such as dichloromethane, 1,2-dichloroethane or halogenated aromatic solvents like chlorobenzene, o-dichlorobenzene.

The solvent used for purification is selected from alkanol such as methanol, ethanol, isopropanol, alkanol-water mixture:

In Japanese Patent Application Laid Open No. Heisei 9 (1997)-40635, a process in which, 2,4'-dihydroxydiphenyl sulfone is separated from an aqueous solution containing 4,4'-dihydroxydiphenyl sulfone and 2,4'-dihydroxydiphenyl sulfone by treating with alkali metal hydroxide. 2,4'-dihydroxydiphenylsulfone is dissolved as a dialkali metal salt and 4,4'-dihdroxydiphenyl sulfone is separated as a monoalkali metal salt. However, in this process, sodium hydroxide and sulfuric acid are to be used in large amounts thereby increasing the cost of the process.

In contrast to the above mentioned prior art the present invention suitably uses aqueous alkanol for the purification of 2,4'- and 4,4'-dihydroxydiphenyl sulfone making up the process cost effective and industrially applicable.

U.S. Pat. No. 2,224,964 describe a process of manufacturing aromatic sulfones wherein diphenyl sulfone was synthesized by condensing benzenesulfonyl chloride with the benzene in the presence of iron chloride, according to the usual Friedel-crafts procedures. This scheme suffers evolution of hydrogen chloride gas.

U.S. Pat. No. 2,000,061 describes a process for the manufacture of a diaryl sulfone by reaction of a volatile aryl compound, having at least one carbon-hydrogen group in the aromatic ring, in vapor phase with sulfur trioxide. This scheme suffers from the shortcoming that one of the byproduct benzenesulofonic acid is toxic.

U.S. Pat. No. 3,052,708 discloses a process for the preparation of aromatic sulfones, wherein diphenyl sulfone was syntheses by reacting two moles of anhydrous benzene with one mole of sulfuric anhydride in one mole of dimethyl pyrosulfate at 70 to 75° C., yielded 83% pure diphenyl sulfone.

U.S. Pat. No. 4,482,742 discloses a process for preparation of 3,3'-diamino diphenyl sulfones by catalytically reducing and dehalogenating, in the presence of a reduction catalyst and a dehalogenating agent.

U.S. Pat. No. 5,399,772 describes a method of producing a 2,4'-dihydroxydiphenyl sulfone by reacting one or more phenols and sulfuric acid in the presence of at least one of phosphoric acid, phosphinic acid and salts thereof, in the absence of a solvent or in present of an aromatic hydrocarbon solvent. In this process obtained mixture of 4,4'-dihydroxydiphenyl sulfone and 2,4'-dihyroxydiphenyl sulfone in weight ratio of 50:50, which is further isolated by treating with mixed solvent containing 5 to 20 w % of at least one lower aliphatic alcohol and 95 to 80 w % of at least one aromatic hydrocarbon which does not contain halogen.

U.S. Pat. No. 5,767,318 describes a process for producing a high purity 2,4'-dihydroxydiphenyl sulfone wherein a mixture of 4,4'-dihydroxydiphenyl sulfone and 2,4'-dihyroxydiphenyl sulfone in weight ratio of 50:50 are obtained by reacting phenol with sulfuric acid in presence of phosphoric acid at 150 to 165° C. under reduced pressure of 560 to 260 mm Hg and separating the products by addition of alkali metal hydroxide and treated with acid.

U.S. Pat. No. 5,288,913 describe a process for the preparation of 4,4'-dihydroxydiphenyl sulfone by reacting of phenol with sulfonating agent in isomeric chlorotoluenes as the inert solvent.

In German offenlegungsschrift No. 3732401, 4,4'-dihydroxydiphenyl sulfone prepared by reacting phenol with sulfonating agent and removing water from the reaction using molybedic and tungstic acid or hetropoly acids as a condensation catalyst.

U.S. Pat. No. 4,820,831 describes the process for preparing 4,4'-dihydroxydiphenyl sulfone by reacting phenol with sulfonating agent or phenolsulfonic acid to a dehydration reaction in the presence of a solvent.

US patent application US 2005/0049437 A1 and WO 03/062194 A1, and EP 1468987 B1, describe a process for producing 2,4'-dihydroxydiphenyl sulfone wherein a mixture of 2,4'-dihydroxydiphenyl sulfone, 4,4'-dihydroxydiphenyl sulfone, phenolsulfonic acid and phenol is obtained by dehydration of phenol and sulfuric acid or phenolsulfonic acid and separating the products by crystallization with adding phenol and mixture of phenol-water.

EP patent 0627415 A1 discloses a process for the production of pure 2,4'-dihydroxydiphenyl sulfone by separating from a mixture containing 4,4'-dihydroxydiphenyl sulfone, 2,4'-dihydroxydiphenyl sulfone by treating with mixed solvents (alcohols/aromatic hydrocarbons, ketones/aromatic hydrocarbons, acetic acid esters/aromatic hydrocarbons).

Japanese Patent Application Laid Open No. Heisei 10 (1998)-25277, discloses the reaction of phenol and a sulfonating agent in presence of solvent, o-dichlorobenzene which produces a mixture of 2,4'-dihydroxydiphenyl sulfone and 4,4'-dihydroxydiphenyl sulfone and which are separated by adjusting phenol concentration.

Japanese Patent Application Laid Open No. Heisei 9 (1997)-40635 discloses a process in which, separating 2,4'-dihydroxydiphenyl sulfone from the aqueous solution containing 4,4'-dihydroxydiphenyl sulfone and 2,4'-dihydroxydiphenyl sulfone by treating with alkali metal hydroxide. 2,4'-dihydroxydiphenylsulfone is dissolved as a dialkali metal salt and 4,4'-dihydroxydiphenyl sulfone is separated as a monoalkali metal salt.

Japanese Patent Application Laid Open No. Showa 50 (1975)-106936 discloses a process in which the product of the reaction between phenol and sulfuric acid is treated with aqueous phenol having to crystallize 4,4'-dihydroxydiphenyl sulfone.

CA 54:P15975, describes preparation of p,p'-dihydroxydiphenyl sulfone from chlorobenzene. This method comprises the hydrolysis of p,p'-diaminodiphenyl sulfone with dilute sulfuric acid at 200° C. to obtained p,p'-dihydroxydiphenyl sulfone with 100% yield.

The process of the preparation of diphenyl sulfone; 2,4'-dihydroxydiphenyl sulfone; and 4,4'-dihydroxydiphenyl sulfone of the present invention differs from published methods in various ways including:

In prior art of diphenyl sulfone, product has been produced by the reaction of benzene with sulfur trioxide or reaction of benzenesulfonyl chloride with benzene but in the present invention diphenyl sulfone is produced by catalytic dehalogenation of isomeric mixture of dichlorodiphenyl sulfone. The dehalogenating reaction of isomeric mixture of dichlorodiphenyl sulfone is carried out in hydrogen in the presence of a reduction catalyst and dehydrohalogenating agent in a temperature range of 20-200° C. and at atmospheric pressure to 50 Bar. The crude diphenyl sulfone is purified by treating with an oxidizing agent and re-crystallization in halogenated hydrocarbons.

In prior art of 2,4'-dihydroxydiphenyl sulfone and 4,4'-dihydroxydiphenyl sulfone, the products have been synthesized by reacting phenol with sulfonating agent and separating by treating with alkali metal salts or solvents or adjusting phenol concentration, herewith in present invention 2,4'-dihydroxydiphenyl sulfone and 4,4'-dihydroxydiphenyl sulfone have been synthesized by hydrolyzing the isomeric mixture of dichlorodiphenyl sulfones at temperatures between 100° C. to 300° C. followed by treatment with dilute sulfuric acid to obtain a mixture of 4,4' and 2,4'-dihydroxydiphenyl sulfone which is further pH adjusted to separate the two isomers which are then recrystallized in alkanol.

The invention is now illustrated with reference to the following non-limiting examples.

EXAMPLE 1

Preparation of Crude 4,4'-Dichlorodiphenyl Sulfone in which Sulfur Trioxide is Added to Dimethyl Sulfate in Step 1

400 g of sulfur trioxide was added to 315 g of dimethyl sulfate in about 1 hour, while maintaining the reaction mixture at 28° C. to 30° C. and maintained for 30 minutes followed by addition of 1.0 g boric acid and allowed to react for 30 minutes. This reaction mixture was added to 562 g of monochlorobenzene in about 1 hour at 30° C. to 35° C. and maintained for 1 hour.

The reaction mixture is then added to 600 g of isopropanol to precipitate 4,4'-dichlorodiphenylsulfone. The precipitate was separated and neutralized with caustic soda lye and repeatedly washed with water and dried to obtain 577 g of the product (APHA of 217). The yield was 80.4% with respect to monochlorobenzene. HPLC analysis showed that the product composition was 98.99% of 4,4'-dichlorodiphenyl sulfone, 0.39% of 3,4'-isomer and 0.68% of 2,4'-isomer. The yield of 4,4'-dichlorodiphenyl sulfone is 79.5% with respect to monochlorobenzene.

EXAMPLE 2

Purification of Crude 4,4'-Dichlorodiphenyl Sulfone in which Sequestering Agent is Used 577 g of crude 4,4'-dichlorodiphenyl sulfone was dissolved in 1160 g 1:1 mixture of chlorobenzene and water at 85° C. to 95° C. The resultant solution was treated with 1.2 g of a sequestering agent followed by separation of the aqueous layer. This step was repeated and solvent layer was filtered off at 85° C. to 95° C. The filtrate was cooled to 30° C. to precipitate pure 4,4'-dichlorodiphenyl sulfone which was separated and washed with water and dried to obtain 542 g the product (APHA of 8). The yield was 75.6% with respect to monochlorobenzene. HPLC analysis showed that the product composition was 99.86% of 4,4'-dichlorodiphenylsulfone, 0.063% of 3,4'-isomer and 0.058% of 2,4'-isomer. The yield of 4,4'-dichlorodiphenyl sulfone is 75.5% with respect to monochlorobenzene.

EXAMPLE 3

Purification of Crude 4,4'-Dichlorodiphenyl Sulfone with Activated Carbon 400 g of sulfur trioxide was added to 315 g of dimethyl sulfate in about 1 hour, while maintaining the reaction mixture at 28° C. to 30° C. and maintained for 30 minutes followed by addition of 1.0 g boric acid and allowed to react for 30 minutes. This reaction mixture was added to 562 g of monochlorobenzene in about 1 hour at 30° C. to 35° C. and maintained for 1 hour.

The reaction mixture is then added to 600 g of isopropanol to precipitate 4,4'-dichlorodiphenylsulfone. The precipitate was separated and neutralized with caustic soda lye and repeatedly washed with water and dried to obtain 570 g of the product (API-IA of 237). The yield was 79.5% with respect to monochlorobenzene. HPLC analysis showed that the product composition was 98.53% of 4,4'-dichlorodiphenyl sulfone, 0.40% of 3,4'-isomer and 1.04% of 2,4'-isomer. The yield of 4,4'-dichlorodiphenyl sulfone is 78.3% with respect to monochlorobenzene.

570 g of crude 4,4'-dichlorodiphenyl sulfone was dissolved in 1160 g 1:1 mixture of chlorobenzene and water at 85° C. to 95° C., followed by separation of the aqueous layer. Then the organic solution was treated with 1.5 g of activated carbon at 80-90° C. for 1 hr and filtered off at 85° C. to 95° C. The filtrate was cooled to 30° C. to precipitate pure 4,4'-dichlorodiphenyl sulfone which was separated and washed with water and dried to obtain 531 g of the product (APHA of 14). The yield was 74.5% with respect to monochlorobenzene. HPLC analysis showed that the product composition was 99.91% of 4,4'-dichlorodiphenylsulfone, 0.047% of 3,4'-isomer and 0.036% of 2,4'-isomer. The yield of 4,4'-dichlorodiphenyl sulfone is 74.4% with respect to monochlorobenzene.

EXAMPLE 4

Purification of Crude 4,4'-Dichlorodiphenyl Sulfone with Sequestering Agent and Activated Carbon 400 g of sulfur trioxide was added to 315 g of dimethyl sulfate in about 1 hour, while maintaining the reaction mixture at 28° C. to 30° C. and then maintained for 30 minutes followed by addition of 1.0 g boric acid and allowed to react for 30 minutes. This reaction mixture was added to 562 g of monochlorobenzene in about 1 hour at 30° C. to 35° C. and maintained for 1 hour.

The reaction mixture is then added to 600 g of isopropanol to precipitate 4,4'-dichlorodiphenylsulfone. The precipitate was separated and neutralized with caustic soda lye and repeatedly washed with water and dried to obtain 569 g the product (APHA of 222). The yield was 79.3% with respect to monochlorobenzene. HPLC analysis showed that the product composition was 98.98% of 4,4'-dichlorodiphenyl sulfone, 0.28% of 3,4'-isomer and 0.69% of 2,4'-isomer. The yield of 4,4'-dichlorodiphenyl sulfone is 78.5% with respect to monochlorobenzene.

569 g of crude 4,4'-dichlorodiphenyl sulfone was dissolved in 1160 g of 1:1 mixture of chlorobenzene and water at 85° C. to 95° C. The resultant solution was treated with 1.2 g of a sequestering agent followed by separation of the aqueous layer. Then the organic solution was treated with 1.5 g of activated carbon at 80-90° C. for 1 hr and filtered off at 85° C. to 95° C. This step was repeated and solvent layer was filtered off at 85° C. to 95° C. The filtrate was cooled to 30° C. to precipitate pure 4,4'-dichlorodiphenyl sulfone which was separated and washed with water and dried to obtain 537 g of the product (APHA of 5). The yield was 74.9% with respect to monochlorobenzene. HPLC analysis showed that the product composition was 99.93% of 4,4'-dichlorodiphenylsulfone, 0.037% of 3,4'-isomer and 0.030% of 2,4'-isomer.

EXAMPLE 5

Recovery of Solvent Isopropanol and Dichlorodiphenyl Sulfone 1330 g water, contain water washing liquor from example 1 and 2 was added to 1135 g residual filtrate, mother liquor from example 1. The resultant mixture was heated to 110° C. and 716 g isopropanol was collected containing 19.8% water. After the removal of isopropanol the precipitate of dichlorodiphenyl sulfone was separated, washed with water and dried to obtain 47 g of product (APHA of 224). The yield was 6.5% with respect to monochlorobenzene. HPLC analysis showed that the product composition was 30.34% of 4,4'-dichlorodiphenyl sulfone, 7.00% of 3,4'-isomer and 60.73% of 2,4'-isomer. The yield of 4,4'-dichlorodiphenyl sulfone is 1.9% with respect to monochlorobenzene.

EXAMPLE 6

Recovery of Monochlorobenzene 1735 g residual liquor from example 5 was hydrolyzed at 180° C. to 230° C. and an azeotropic mixture of monochlorobenzene and water was formed, which was isolated in Dean and Stark assembly and 38 g chlorobenzene with 0.6% moisture was collected.

EXAMPLE 7

Recovery of Sulfuric Acid 619 g residual liquor from example 6 was concentrated by applying 0.2 mm·hg vacuum (0.5 mm·Hg) at 170° C. and 458 g dark brown sulfuric acid of 92.3% purity was obtained. Then 70 g hydrogen peroxide, 50% by weight was added to this in 1 hour at 140° C. to 150° C. and a clear pale yellow straw in color of sulfuric acid of 86.2% purity was obtained.

EXAMPLE 8

Preparation of Crude 4,4'-Dichlorodiphenyl Sulfone in which Addition of Catalyst to Sulfur Trioxide in Step 2

1.0 g boric acid was added to 400 g of sulfur trioxide at 28° C. to 30° C. and further the resultant mixture was added to 315 g of dimethyl sulfate in about 1 hour, while maintaining the reaction mixture at 28° C. to 30° C. and then maintained for 1 hour. This reaction mixture was added to 562 g of monochlorobenzene in about 1 hour at 30° C. to 35° C. and maintained for 1 hour.

The reaction mixture is then added to 600 g of isopropanol to precipitate 4,4'-dichlorodiphenyl sulfone. The precipitate was separated and neutralized with caustic soda lye and repeatedly washed with water and dried to obtain 491 g of the product. The yield was 68.5% with respect to monochlorobenzene. HPLC analysis showed that the product composition was 98.28% of 4,4'-dichlorodiphenyl sulfone, 0.28% of 3,4'-isomer and 0.90% of 2,4'-isomer. The yield of 4,4'-dichlorodiphenyl sulfone is 67.3% with respect to monochlorobenzene.

EXAMPLE 9

Preparation of Crude 4,4'-Dichlorodiphenyl Sulfone in which Addition of Catalyst to Dimethyl Sulfate in Step 2

400 g of sulfur trioxide was added to mixture of 1 g boric acid and 315 g of dimethyl sulfate in about 1 hour, while maintaining the reaction mixture at 28° C. to 30° C. and maintained for 1 hour. This reaction mixture was added to 562 g of monochlorobenzene, in about 1 hour at 30° C. to 35° C. and maintained for 1 hour.

The reaction mixture is then added to 600 g of isopropanol to precipitate 4,4'-dichlorodiphenyl sulfone. The precipitate was separated and neutralized with caustic soda lye and repeatedly washed with water and dried to obtain 515 g of the product. The yield was 71.8% with respect to monochlorobenzene. HPLC analysis showed that the product composition was 98.97% of 4,4'-dichlorodiphenyl sulfone, 0.24% of 3,4'-isomer and 0.74% of 2,4'-isomer. The yield of 4,4'-dichlorodiphenyl sulfone is 71.1% with respect to monochlorobenzene.

EXAMPLE 10

Preparation of Crude 4,4'-Dichlorodiphenyl Sulfone in which Addition of Catalyst to Chlorobenzene in Step 3

400 g of sulfur trioxide was added to 315 g of dimethyl sulfate in about 1 hour, while maintaining the reaction mixture at 28° C. to 30° C. and then maintained for 1 hour. This reaction mixture was added to 562 g of monochlorobenzene which contains 1 g boric acid, in about 1 hour at 30° C. to 35° C. and maintained for 1 hour.

The reaction mixture is then added to 600 g of isopropanol to precipitate 4,4'-dichlorodiphenyl sulfone. The precipitate was separated and neutralized with caustic soda lye and repeatedly washed with water and dried to obtain 466 g of product. The yield was 65.0% with respect to monochlorobenzene. HPLC analysis showed that the product composition was 96.80% of 4,4'-dichlorodiphenyl sulfone, 0.52% of 3,4'-isomer, 0.87% of 2,4'-isomer and 1.47% unknown. The yield of 4,4'-dichlorodiphenyl sulfone is 62.9% with respect to monochlorobenzene.

EXAMPLE 11

Preparation of Crude 4,4'-Dichlorodiphenyl Sulfone in which Addition of Catalyst in Mixture of Dimethyl Sulfate, Sulfur Trioxide and Chlorobenzene in Step 3

400 g of sulfur trioxide was added to 315 g of dimethyl sulfate in about 1 hour, while maintaining the reaction mixture at 28° C. to 30° C. and maintained for 1 hour. This reaction mixture was added to 562 g of monochlorobenzene in about 1 hour at 30° C. to 35° C. and followed by added 1 g boric acid in it and maintained for 1 hour.

The reaction mixture is then added to 600 g of isopropanol to precipitate 4,4'-dichlorodiphenylsulfone. The precipitate was separated and neutralized with caustic soda lye and repeatedly washed with water and dried to obtain 488 g of product. The yield was 68.0% with respect to monochlorobenzene. HPLC analysis showed that the product composition was 99.46% of 4,4'-dichlorodiphenyl sulfone, 0.18% of 3,4'-isomer and 0.29% of 2,4'-isomer. The yield of 4,4'-dichlorodiphenyl sulfone is 67.6% with respect to monochlorobenzene.

Table 1 presents the results of examples nos. 1 and 8 to 11.

TABLE 1 order of addition of catalyst

| | | % yield of dichlorodiphenyl sulfone | | | |
|---|---|---|---|---|---|
| | | | HPLC Data | | |
| Ex. No. | Catalyst added to | Total | 4,4'-isomer | 3,4'-isomer | 2,4'-isomer |
| 1 | Mixture of 2 moles sulfur trioxide and one mole dimethyl sulfate | 80.4 | 98.99 | 0.39 | 0.68 |
| 8 | 2 mole Sulfur trioxide | 68.5 | 98.28 | 0.28 | 0.90 |
| 9 | 1 mole dimethyl sulfate | 71.8 | 98.97 | 0.24 | 0.74 |
| 10 | 2 moles Monochlorobenzene | 65.0 | 96.80 | 0.52 | 0.87 |
| 11 | Mixture of 2 moles sulfur trioxide, one mole dimethyl sulfate and two mole Monochlorobenzene. | 68.0 | 99.46 | 0.18 | 0.29 |

It is clear from examples 1 & 8-11 that the addition of catalyst to the mixture of one mole of dimethyl sulfate and two mole of sulfur trioxide gives a yield of 80.4% with 98.99% selectivity of 4,4'-dichlorodiphenyl sulfone.

EXAMPLE 12

Preparation of Crude 4,4'-Dichlorodiphenyl Sulfone in which Dimethyl Sulfate is Added to Sulfur Trioxide in Step 1

315 g of dimethyl sulfate was added to 400 g of sulfur trioxide in about 1 hour, while maintaining the reaction mixture at 28° C. to 30° C. and maintained for 30 minutes followed by addition of 1.0 g boric acid which was allowed to react for 30 minutes. This reaction mixture was added to 562 g of monochlorobenzene in about 1 hour at 30° C. to 35° C. and then maintained for 1 hour.

The reaction mixture is then added to 600 g of water to precipitate 4,4'-dichlorodiphenylsulfone. The precipitate was separated and neutralized with caustic soda lye and repeatedly washed with water and dried to obtain 485 g of product. The yield was 67.6% with respect to monochlorobenzene. HPLC analysis showed that the product composition was 96.45% of 4,4'-dichlorodiphenyl sulfone, 0.54% of 3,4'-isomer and 2.91% of 2,4'-isomer. The yield of 4,4'-dichlorodiphenyl sulfone is 65.2% with respect to monochlorobenzene.

EXAMPLE 13

Preparation of Crude 4,4'-Dichlorodiphenyl Sulfone in which Simultaneous Addition of Dimethyl Sulfate and Sulfur Trioxide in Step 1

315 g of dimethyl sulfate and 400 g of sulfur trioxide was mixed by simultaneous addition for about 1 hour, while maintaining the reaction mixture at 28° C. to 30° C. and then maintained for 30 minutes followed by addition of 1.0 g boric acid and allowed to react for 30 minutes. This reaction mixture was added to 562 g of monochlorobenzene in about 1 hour at 30° C. to 35° C. and maintained for 1 hour.

The reaction mixture is then added to 600 g of water to precipitate 4,4'-dichlorodiphenylsulfone. The precipitate was separated and neutralized with caustic soda lye and repeatedly washed with water and dried to obtain 602 g the product. The yield was 84.0% with respect to monochlorobenzene. HPLC analysis showed that the product composition was 94.63% of 4,4'-dichlorodiphenyl sulfone, 0.71% of 3,4'-isomer and 4.54% of 2,4'-isomer. The yield of 4,4'-dichlorodiphenyl sulfone is 79.4% with respect to monochlorobenzene.

EXAMPLE 14

Preparation of Crude 4,4'-Dichlorodiphenyl Sulfone in which Sulfur Trioxide is Added to Dimethyl Sulfate in Step 1 and Use of Water as a Solvent in Place of Isopropanol The procedure was similar to that for Example 1 except that reaction mixture was poured to 600 g water. After following the steps, 620 g the product was obtained. The yield was 86.4% with respect to monochlorobenzene. HPLC analysis showed that the product composition was 94.28% of 4,4'-dichlorodiphenyl sulfone, 0.70% of 3,4'-isomer and 4.88% of 2,4'-isomer. The yield of 4,4'-dichlorodiphenyl sulfone is 81.5% with respect to monochlorobenzene. Table 2 presents the results examples Nos. 12-14.

TABLE 2 order of addition of dimethyl sulfate and sulfur trioxide in step 1

| | | % yield of dichlorodiphenyl sulfone | | | |
|---|---|---|---|---|---|
| | | | HPLC Data | | |
| Ex. No. | Order of addition | Total | 4,4'-isomer | 3,4'-isomer | 2,4'-isomer |
| 12 | 1 mole dimethyl sulfate to 2 moles sulfur trioxide | 67.6 | 96.45 | 0.54 | 2.91 |
| 13 | Simultaneous addition of 2 mole sulfur trioxide and 1 mole dimethyl sulfate | 84.0 | 94.63 | 0.71 | 4.54 |
| 14 | 2 moles sulfur trioxide to 1 mole dimethyl sulfate | 86.4 | 94.28 | 0.70 | 4.88 |

It is clear from examples 12, 13 and 14 that the order of addition of sulfur trioxide and dimethyl sulfate to form the mixture of two moles sulfur trioxide and one mole of dimethyl sulfate has significant impact on yield of 4,4'-dichlorodiphenyl sulfone.

EXAMPLE 15

Preparation of Crude 4,4'-Dichlorodiphenyl Sulfone in which the Recovered Solvent Isopropanol Containing 20% Water is Used This procedure was similar to that for Example 1 except that reaction mixture was poured to 716 g isopropanol containing 19.8% water. After following the steps in example 1, 565 g the product (APHA of 263) was obtained. The yield was 78.8% with respect to monochlorobenzene. HPLC analysis showed that the product composition was 98.64% of 4,4'-dichlorodiphenyl sulfone, 0.32% of 3,4'-isomer and 0.90% of 2,4'-isomer. The yield of 4,4'-dichlorodiphenyl sulfone is 77.7% with respect to monochlorobenzene.

EXAMPLE 16

Preparation of Crude 4,4'-Dichlorodiphenyl Sulfone in which Use of Methanol as a Solvent in Place of Isopropanol The procedure was similar to that for Example 1 except that reaction mixture was poured to 600 g methanol. After following the steps 510 g the product was obtained. The yield was 71.1% with respect to monochlorobenzene. HPLC analysis showed that the product composition was 98.70% of 4,4'-dichlorodiphenyl sulfone, 0.26% of 3,4'-isomer and 1.02% of 2,4'-isomer. The yield of 4,4'-dichlorodiphenyl sulfone is 70.2% with respect to monochlorobenzene.

EXAMPLE 17

Preparation of Crude 4,4'-Dichlorodiphenyl Sulfone in which Use of Monochlorobenzene as a Solvent in Place of Isopropanol The procedure was similar to that for Example 1 except that reaction mixture was poured to mixture of 600 g monochlorobenzene and 300 g water. After following the steps, 395 g the product was obtained. The yield was 55.1% with respect to monochlorobenzene. HPLC analysis showed that the product composition was 99.77% of 4,4'-dichlorodiphenyl sulfone, 0.13% of 3,4'-isomer and 0.073% of 2,4'-isomer. The yield of 4,4'-dichlorodiphenyl sulfone is 54.97% with respect to monochlorobenzene.

EXAMPLE 18

Preparation of Crude 4,4'-Dichlorodiphenyl Sulfone in which Use of 1,2-Dichloroethane as a Solvent in Place of Isopropanol The procedure was similar to that for Example 1 except that reaction mixture was poured to 600 g of 1,2-dichloroethane. After following the steps, 302 g the product was obtained. The yield was 42.1% with respect to monochlorobenzene. HPLC analysis showed that the product composition was 96.1% of 4,4'-dichlorodiphenyl sulfone, 0.42% of 3,4'-isomer and 1.78% of 2,4'-isomer and 1.69% unknown. The yield of 4,4'-dichlorodiphenyl sulfone is 40.4% with respect to monochlorobenzene.

Table 3 presents the results of example nos. 1, 14-18

TABLE 3 selectivity of solvent for separation of 4,4'-dichlorodiphenyl sulfone from reaction mixture in step 5

| Ex. No. | Solvent | % yield of dichlorodiphenyl sulfone | | | |
|---|---|---|---|---|---|
| | | | HPLC Data | | |
| | | Total | 4,4'-isomer | 3,4'-isomer | 2,4'-isomer |
| 1 | Isopropanol | 80.4 | 98.99 | 0.39 | 0.68 |
| 14 | Water | 86.4 | 94.28 | 0.70 | 4.88 |
| 15 | Isopropanol-water mixture | 78.8 | 98.64 | 0.32 | 0.90 |
| 16 | Methanol | 71.1 | 98.70 | 0.26 | 1.02 |
| 17 | Chlorobenzene | 55.1 | 99.77 | 0.13 | 0.073 |
| 18 | 1,2-dichloroethane | 42.1 | 96.1 | 0.42 | 1.78 |

JP 09157246 discloses a process for isolating 4,4'-dichloro diphenyl sulfone by crystallization by dissolving a mixture of 4,4'-dichloro diphenyl sulfone and sulfuric acid in organic solvent and water. The yield of dichlorodiphenyl sulfone is 73.3% on basis of chlorobenzene used and purity of 4,4'-dichlorodiphenyl sulfone is 99.88%.

In contrast the process of the present invention in which isopropanol used for separation of 4,4'-dichlorodiphenyl sulfone gives a yield of 80.4% with 98.99% selectivity for 4,4' dichlorodiphenyl sulfone isomer in this stage.

EXAMPLE 19

Preparation of Crude 4,4'-Dichlorodiphenyl Sulfone in which Reaction Temperature is 50 to 75° C. in Place of 28 to 35° C.

400 g of sulfur trioxide was added to 315 g of dimethyl sulfate in about 1 hour, while maintaining the reaction mixture at 70° C. to 75° C. and then maintained for 30 minutes followed by addition of 1.0 g boric acid and allowed to react for 30 minutes. This reaction mixture was added to 562 g of monochlorobenzene in about 1 hour at 50° C. to 55° C. and maintained for 1 hour.

The reaction mixture is then added to 600 g of isopropanol to precipitate 4,4'-dichlorodiphenyl sulfone. The precipitate was separated and neutralized with caustic soda lye and repeatedly washed with water and dried to obtain 561 g the product (APHA of 192). The yield was 78.2% with respect to monochlorobenzene. HPLC analysis showed that the product composition was 98.02% of 4,4'-dichlorodiphenyl sulfone, 0.43% of 3,4'-isomer and 1.12% of 2,4'-isomer. The yield of 4,4'-dichlorodiphenyl sulfone is 76.7% with respect to monochlorobenzene.

Table 4 represents the results of examples 1 and 19.

TABLE 4

Selection of temperature parameters:

| Ex. No. | Temperature range | % yield of dichlorodiphenyl sulfone | | | |
|---|---|---|---|---|---|
| | | | HPLC Data | | |
| | | Total | 4,4'-isomer | 3,4'-isomer | 2,4'-isomer |
| 1 | 28° to 35° C. | 80.4 | 98.99 | 0.39 | 0.68 |
| 19 | 50° to 75° C. | 78.2 | 98.02 | 0.43 | 1.12 |

Temperature has a significant effect on yield and selectivity of 4,4'-dichlorodiphenyl sulfone in step 1, 2 and 3.

EXAMPLE 20

Conversion of Isomeric Mixture of Dichlorodiphenyl Sulfones to Diphenyl Sulfone by Method (A)

200 g isomeric mixture of dichlorodiphenyl sulfones was dissolved in 1000 ml methyl cellosolve and treated with carbon at 90° C. The treated mixture was filtered off and used for hydrogenation. 300 ml triethyl amine was added in the reaction mixture, with the further addition of 40 g of appropriately selected Raney Nickel catalyst. Hydrogen is introduced under stirring at temperatures of 90° C. and a pressure of 5.0 bars for 50 hrs. The reaction solution is filtered at 90° C. to remove the catalyst and the solvent is extracted by distillation and then allowed to cool giving light brown crystals which were filtered, washed with water to neutralize and then dried. 158 g of the mixture was obtained containing 81.66% diphenyl sulfone, 17.49% 2-chlorodiphenyl sulfone and 0.30% 4-chlorodiphenyl sulfone. Further this dried mixture is dissolved in 200 ml chlorobenzene at 90° C. and treated with 5 g of 30% hydrogen peroxide and allowed to cool. A precipitate obtained was filtered, washed with water to neutralize and re-crystallized in chlorobenzene and treated with activated carbon giving white crystals of diphenyl sulfone; 103 g of product was obtained containing 99.672% of diphenyl sulfone.

EXAMPLE 21

Conversion of Isomeric Mixture of Dichlorodiphenyl Sulfones to Diphenyl Sulfone and 2-Aminodiphenyl Sulfone by Method (A)

574 g isomeric mixture of dichlorodiphenyl sulfones was dissolved in 1500 ml methyl cellosolve and treated with activated carbon at 90° C. The treated mixture was filtered off and used for hydrogenation. 600 ml triethyl amine and 115 g Raney Nickel catalyst was added to this reaction mixture. Hydrogen is introduced under stirring at temperatures of 30-35° C. and maintaining pressure at 5.0 bar at 90 to 95° C. for 20 hrs. The reaction solution is filtered at 70 to 80° C. to remove the catalyst. Further, the solvent is removed by distillation and the residue is then allowed to cool giving light brown crystals which are filtered, washed with water to neutralize and dried to get 452 g of product containing 49.80% diphenyl sulfone, 38.62% 2-chlorodiphenyl sulfone and 9.69% 4-chlorodiphenyl sulfone.

The obtained 452 g isomeric mixture of diphenyl sulfone and monochlorodiphenyl sulfones is ammonolyzed with 1650 g liquor ammonia at 220° C. for 6 hours in presence of 22 g cuprous chloride as a catalyst. After completion of the reaction, the mixture is cooled to room temperature and the formed precipitate is filtered, washed with water to neutralize and then dried. 382 g of mixture was obtained containing 58.32% diphenyl sulfone, 36.48% 2-aminodiphenyl sulfone and 5.38% 4-aminodiphenyl sulfone.

The obtained 382 g isomeric mixture of diphenyl sulfone, 2-aminodiphenyl sulfone and 4-aminodiphenyl sulfone is treated with a mixture of 600 ml methanol and 50 g concentrated hydrochloric acid under reflux for 30 mins and cooled to 30° C., filtered, washed with water to neutralize and re-crystallized in chlorobenzene with activated carbon treatment giving white crystals of diphenyl sulfone; 186 g of product was obtained containing 88.79% diphenyl sulfone, 8.03% 2-aminodiphenyl sulfone and 0.532% 4-aminodiphenyl sulfone. Then the organic solvent is washed with water and separated from the aqueous layer. The solvent is then recovered by distillation; 178 g residue is then obtained. HPLC analysis showed that this residue is composed of 30.27% diphenyl sulfone, 58.12% 2-aminodiphenyl sulfone and 1.26% 4-aminodiphenyl sulfone. The residue is again dissolved in 300 g of 70% aqueous methanol and maintained under reflux for 30 mins then cooled to 30° C., filtered, washed with water and this step was repeated twice, 106 g of product was obtained. HPLC analysis showed that the product composition was 16.44% diphenyl sulfone and 81.21% of 2-aminodiphenyl sulfone.

EXAMPLE 22

Isolation of Diphenyl Sulfone and Monochlorodiphenyl Sulfones from Mixture Thereof and Conversion of 2-Chlorodiphenyl Sulfone to 2-Aminodiphenyl Sulfone by Method (A)

574 g isomeric mixture of dichlorodiphenyl sulfone was dissolved in 1500 ml methyl Cellosolve and treated with activated carbon at 90° C. The treated mixture was filtered off and used for hydrogenation. 600 ml triethyl amine and 115 g Raney Nickel catalyst was added to this reaction mixture. Hydrogen is introduced under stirring at temperatures of 30-35° C. and maintaining pressure at 5.0 bar at 90 to 95° C. for 20 hrs. The reaction solution is filtered at 90° C. to remove the catalyst and the solvent is extracted by distillation and then allowed to cool giving light brown crystals which are filtered, washed with water to neutralize and then dried. 460 g of product was obtained containing 42.96% diphenyl sulfone, 37.63% 2-chlorodiphenyl sulfone and 15.71% 4-chlorodiphenyl sulfone. Further the solid is dissolved in 400 ml chlorobenzene at 90° C. and treated with 5 g of 30% hydrogen peroxide and allowed to cool. The precipitate obtained was filtered, washed with water to neutralize and re-crystallized in chlorobenzene with activated carbon treatment giving white crystals of diphenyl sulfone; 128 g of product was obtained containing 99.56% of diphenyl sulfone. Mother liquor is removed by distillation to obtain 280 g of residue containing 19.48% diphenyl sulfone, 56.8% 2-chlorodiphenyl sulfone and 23.6% 4-chlorodiphenyl sulfone.

The obtained 280 g isomeric mixture of diphenyl sulfone and monochlorodiphenyl sulfones is ammonolyzed with 1000 g liquor ammonia at 220° C. for 6 hours in presence of 15 g cuprous chloride as a catalyst. After completion of the reaction, the mixture is cooled to room temperature and the formed precipitate is filtered, washed with water to neutralize and then dried, 248 g of product was obtained containing 21.35% diphenyl sulfone, 56.16% 2-aminodiphenyl sulfone and 21.57% 4-aminodiphenyl sulfone.

The obtained 248 g isomeric mixture of diphenyl sulfone, 2-aminodiphenyl sulfone and 4-aminodiphenyl sulfone is treated with a mixture of 350 ml methanol and 50 g concentrated hydrochloric acid under reflux for 30 mins and cooled to 30° C., filtered, washed with water to neutralize and recrystallized in chlorobenzene with activated carbon treatment giving white crystals of diphenyl sulfone; 68 g of dried product was obtained containing 76.19% diphenyl sulfone, 14.52% 2-aminodiphenyl sulfone and 4.37% 4-aminodiphenyl sulfone. Then the organic solvent is washed with water and separated from the aqueous layer. Further, the solvent is recovered by distillation; 142 g residue is obtained. HPLC analysis showed that the residue composition was 8.35% diphenyl sulfone, 76.25% 2-aminodiphenyl sulfone and 14.01% 4-aminodiphenyl sulfone. This was again dissolved in 300 g of 70% aqueous methanol under reflux for 30 mins and cooled to 30° C., filtered, washed with water and this step was repeated. 122 g of product was obtained. HPLC analysis showed that this product composition was 6.76% diphenyl sulfone, 82.44% of 2-aminodiphenyl sulfone and 10.04% 4-aminodiphenyl sulfone.

EXAMPLE 23

Preparation of Crude Dihydroxydiphenyl Sulfone by Method (B)

355 g isomeric mixture of dichlorodiphenyl sulfone containing 31.06%, 52.40% and 15.48% 4,4'-; 2,4'- and 3,4'-dichlorodiphenyl sulfone respectively was placed in a reactor and 644 g caustic soda lye of 50% was added with 1183 g water. The reaction mixture was heated to 220° C. with autogenous pressure and maintained for 4 hours. After completion of reaction, the mixture was filtered out to isolate unreacted dichlorodiphenyl sulfone. The filtrate was treated with dilute sulfuric acid to obtain a precipitate of crude dihydroxydiphenyl sulfone. The precipitate was separated and neutralized by repeatedly washing with water and dried to obtain 240 g of the product. The yield was 77.67% with respect to dichlorodiphenyl sulfone. HPLC analysis showed that the product composition was 34.57% of 4,4'-dihydroxydiphenyl sulfone and 65.0% of 2,4'-dihydroxydiphenyl sulfone.

EXAMPLE 24

Isolation of Pure 2,4' and 4,4'-Dihydroxydiphenyl Sulfone by Method (B)

240 g crude dihydroxydiphenyl sulfone obtained in example 23 was dissolved in 320 g of 25% caustic soda lye under reflux for 2 hours. After the complete dissolution of dihydroxydiphenyl sulfone 17 g sulfuric acid of 98% strength was added and the solution was cooled to 50° C. & pH 10.85, a precipitate of monosodium salt of 4,4'-dihydroxydiphenyl sulfone was removed by filtration.

The filtrate was cooled to 25° C. and 64 g sulfuric acid of 98% strength was added in it while maintaining a pH of 5.0. A precipitate of 2,4'-dihydroxydiphenyl sulfone was removed by filtration thereafter. The obtained product of 2,4'-dihydroxydiphenyl sulfone was dissolved in 960 g of 30% aqueous methanol solution under reflux for 1 hour. Then cooled to 30° C. to obtain the precipitate. This precipitate was separated and repeatedly washed with water and dried to obtain 109 g the product. The yield was 69.87% with respect to available 2,4'-dihydroxydiphenyl sulfone in crude dihydroxydiphenyl mixture. HPLC analysis showed that the product composition was 0.43% of 4,4'-dihydroxydiphenyl sulfone and 99.54% of 2,4'-dihydroxydiphenyl sulfone.

The obtained monosodium salt of 4,4'-dihydroxydiphenyl sulfone was dissolved in 200 ml water and 20 g of sulfuric acid of 98% strength was added in it while maintaining a pH of 5.0. A precipitate of 4,4'-dihydroxydiphenyl sulfone thus formed was removed by filtration.

The obtained product of 4,4'-dihydroxydiphenyl sulfone was dissolved in 300 g of 30% aqueous methanol solution under reflux for 1 hour. This was then cooled to 30° C. and the precipitate was obtained. This precipitate was separated and repeatedly washed with water and dried to obtain 57 g the product. The yield was 68.67% with respect to available 4,4'-dihydroxydiphenyl sulfone in crude dihydroxydiphenyl sulfone mixture. HPLC analysis showed that the product composition was 99.56% of 4,4'-dihydroxydiphenyl sulfone and 0.44% of 2,4'-dihydroxydiphenyl sulfone.

EXAMPLE 25

Preparation of Crude Dihydroxydiphenyl Sulfone in which 54.48% 4,4'-Dichlordiphenyl Sulfone Content in Isomeric Mixture of Dichlorodiphenyl Sulfone by Method (B)

The procedure was similar to that for Example 23 except that the composition of isomeric mixture was used as 54.48%, 35.87% and 9.08% 4,4'-; 2,4'- and 3,4'-dichlorodiphenyl sulfone respectively. After following the steps, 262 g of product was obtained. The yield was 84.79% with respect to dichlorodiphenyl sulfone. HPLC analysis showed that the product composition was 66.26% of 4,4'-dihydroxydiphenyl sulfone and 33.17% of 2,4'-dihydroxydiphenyl sulfone.

EXAMPLE 26

Preparation of Crude Dihydroxydiphenyl Sulfone in which Chlorobenzene is Used in Place of Water by Method (B)

The procedure was similar to that for Example 23 except that the instead of water chlorobenzene was used. After following the steps, 259 g the product was obtained. The yield was 83.82% with respect to dichlorodiphenyl sulfone. HPLC analysis showed that the product composition was 43.65% of 4,4'-dihydroxydiphenyl sulfone and 54.73% of 2,4'-dihydroxydiphenyl sulfone.

EXAMPLE 27

Preparation of Crude Dihydroxydiphenyl Sulfone in which Methanol is Used by Method (B)

The procedure was similar to that for Example 23 with 500 g methanol is used. After following the steps, 194 g of product was obtained. The yield was 62.78% with respect to dichlorodiphenyl sulfone. HPLC analysis showed that the product composition was 40.18% of 4,4'-dihydroxydiphenyl sulfone and 57.68% of 2,4'-dihydroxydiphenyl sulfone.

The present invention provides an economic and environmentally friendly method for the preparation of 4,4'-dichlorodiphenyl sulfone overcoming all the shortcomings of the prior art and achieves the set objectives of providing a process for the preparation of 4,4'-dichlorodiphenyl sulfone:
  Substantially free of 2,4' and 3,4'-isomers of dichlorodiphenyl sulfone;
  With yield of over 90%;
  Polymer grade material;
  With substantially reduced reaction times;
  In which catalysts are used without the need to prepare catalyst impregnated sintered glass or silica balls;
  With enhanced color specifications;
  Wherein no olefins are formed while recovering the alkanol such as Isopropanol;
  Without the production of toxic byproducts such as dimethyl pyrosulfate and reducing the load on effluent treatment plants;
  In which the reactants and byproducts are substantially recycled.

Further the present invention discloses how the isomeric mixture of 4,4'-, 3,4'-, and 2,4'-dichlorodiphenyl sulfone produced during the preparation of 4,4'-dichlorodiphenyl sulfone can be converted into value added products such as diphenyl sulfone, 2,4'-dihydroxydiphenyl sulfone and 4,4'-dihydroxydiphenyl sulfone. Further, the present invention also discloses how the mixture of diphenyl sulfone and monochlorodiphenyl sulfones produced during the catalytic dehalogenation of isomeric mixture of 4,4'-, 3,4'-, and 2,4'-dichlorodiphenyl sulfone can be converted into value added product 2-aminodiphenyl sulfone by ammonolysis.

What is claimed is:
1. A process for the production of 4,4'-dichlorodiphenyl sulfone in steps comprising:
  reacting dimethyl sulfate and sulfur trioxide to form a reaction mixture comprising dimethyl pyrosulfate;
  reacting the formed dimethyl pyrosulfate with unreacted sulfur trixoxide in the reaction mixture;
  reacting the reaction mixture with monochlorobenzene to form an isomeric mixture of dichlorodiphenyl sulfones;
  optionally removing unreacted dimethyl sulfate;
  isolating crude 4,4'-dichlorodiphenyl sulfone using a water miscible alkanol/water miscible alkanol-water mixture;
  recovering the solvent from mother liquor;
  optionally recovering the isomeric mixture of dichlorodiphenyl sulfones from mother liquor;
  optionally, converting the residual isomeric mixture of dichlorodiphenyl sulfones to a product selected from diphenyl sulfone, 2-aminodiphenyl sulfone; 2,4'-dihydroxydiphenyl sulfone, 4,4'-dihydroxydiphenyl sulfone;

optionally recovering monochlorobenzene sulfonic acid and/or monochlorobenzene from the mother liquor;

optionally recovering sulfuric acid from the residual liquor;

optionally recycling the solvent; and purifying 4,4'-dichlorodiphenyl sulfone from crude followed by crystallization and treating with one or more of a sequestering agent or activated carbon in the presence of a water immiscible solvent or a water immiscible solvent-water mixture, wherein catalyst is added in the step of reacting dimethyl sulfate and sulfur trioxide, the step of reacting the formed dimethyl pyrosulfate with unreacted sulfur trioxide, the step of reacting the mixture with monochlorobenzene, or at the end of the step of reacting the mixture with monochlorobenzene.

2. A process according to claim 1 for production of substantially pure 4,4'-dichlorodiphenyl sulfone in steps comprising preparing a mixture of dimethyl pyrosulfate and sulfur trioxide by reacting one mole dimethyl sulfate and two moles of sulfur trioxide to carry out the reaction at 10° C. to 120° C. followed by completion of the reaction in the presence of catalyst, which is further reacted with monochlorobenzene at 10° C. to 120° C. for 30 to 300 minutes followed by treatment with a water miscible alkanol or water miscible alkanol-water mixture at 20° C. to 100° C., cooling, and separating the precipitate to achieve a yield of 80% and a purity of 99% purity 4,4'-dichlorodiphenyl sulfone, wherein the product is further purified using monochlorobenzene to obtain 4,4'-dichlorodiphenyl sulfone of ≥−99.5% purity.

3. A process according to claim 1 wherein the catalyst is added to the mixture of dimethyl pyrosulfate and unreacted sulfur trioxide in the step of reacting dimethyl sulfate and sulfur trioxide.

4. A process according to claim 1 wherein the catalyst is added in the step of reacting dimethyl sulfate and sulfur trioxide, and the step includes adding the catalyst to two moles of sulfur trioxide to form a mixture, and adding the mixture to one mole of dimethyl sulfate.

5. A process according to claim 1 wherein one mole of dimethyl sulfate and two moles of sulfur trioxide are reacted without a catalyst and the step of reacting the reaction mixture with monochlorobenzene comprises reacting the reaction mixture with two moles of monochlorobenzene in the presence of catalyst.

6. A process according to claim 1 wherein a mixture of two moles of sulfur trioxide and one mole of dimethyl sulfate is added to two moles of monochlorobenzene in the step of step of reacting the reaction mixture with monochlorobenzene and the catalyst is added to this mixture after step of reacting the reaction mixture with monochlorobenzene.

7. A process according to claim 1 wherein the catalyst is selected from boron based compounds such as boric acid, boron trioxide or esters of boron based compounds or aluminum trioxide, used in concentrations of 0.01% to 10 mole %, preferably from 0.1% to 5 mole % and most preferably from 0.2% to 2.5 mole % based on one mole sulfur trioxide.

8. A process according claim 1 wherein the unreacted dimethyl sulfate after reaction of dimethyl pyrosulfate and unreacted sulfur trioxide with monochlorobenzene is removed from the reaction mixture by vacuum distillation with a vacuum 0.1 to 5 mm Hg at 120 to 190° C., preferably at 140° C. to 180° C.

9. A process according to claim 1 wherein the water miscible alkanol is selected from methanol, ethanol, isopropanol, isobutanol, the preferred alkanol being isopropanol.

10. A process according to claim 1 wherein the ratio of solvent to the reaction mixture on weight basis is 1:0.2 to 1:2, preferably 1:0.4 to 1:0.6, the ratio of solvent-water mixture to the reaction mixture on weight basis is 1:0.2 to 1:2, preferably 1:0.4 to 1:0.6 with respect to solvent.

11. A process according to claim 1 wherein the solvent is recovered by azeotropic distillation with water by adding water externally in mother liquor in ratio 1:0.5 to 1:3.0, preferably 1:0 to 1:1.5 with reaction mixture at temperature 80° C. to 115° C.

12. A process according to claim 1 wherein purification of crude dichlorodiphenyl sulfone is carried out in steps comprising:

treating with water immiscible solvent-water mixture at 85° C. to 95° C.;

treating with sequestering agent and/or activated carbon at 85° C. to 95° C. in presence of water immiscible solvent or water immiscible solvent-water mixture;

washing the solvent layer with water at 85° C. to 95° C. to remove water soluble impurities;

filtering the solvent layer at 85° C. to 95° C. to remove water insoluble impurities; and cooling the solvent to crystallize the product and filtering the same to isolate the product.

13. A process as claimed in claim 12 wherein the solvent is selected from monochlorobenzene, toluene, trichloroethylene and tetrachloroethylene.

14. A process as claimed in claim 12 wherein the ratio of crude 4,4'-dichlorodiphenyl sulfone with the water immiscible solvent-water mixture on weight basis is 1:1 to 1:4, preferably 1:1.5 to 1:2.5; the ratio of water immiscible solvent with water on weight basis is 1:0.5 to 1:2, preferably 1:0.8 to 1:1.2.

15. A process according to claim 12, wherein the sequestering agent is selected from a range of phosphonic acid compounds and used in concentrations of 0.025% to 5% w/w, preferably 0.1 to 1% w/w based on crude 4,4'-dichlorodiphenyl sulfone.

16. A process according to claim 12, comprising using activated carbon at 0.025% to 5% w/w, preferably 0.1 to 1% w/w based on crude containing at least 90% 4,4'-dichlorodiphenyl sulfone.

17. A process according to claim 1, further comprising conversion of residual isomeric mixture of dichlorodiphenyl sulfones to pure diphenyl sulfone in steps comprising:

a. dissolving isomeric mixture of dichlorodiphenyl sulfones in organic solvent optionally in the presence of activated carbon at 80 to 100° C.;

b. dehalogenating dichlorodiphenyl sulfone in the presence of a catalyst;

c. removing catalyst and solvent from the reaction mixture to obtain a residue containing a mixture of diphenyl sulfone and monochlorodiphenyl sulfones;

d. dissolving the residue of step (c) in halogenated hydrocarbon and treating with oxidizing agent at 80-90° C., cooling to crystallize the diphenyl sulfone, separating the mother liquor and dissolving the diphenyl sulfone in halogenated hydrocarbon followed by carbon treatment at 80-90° C. and cooling to obtain diphenyl sulfone of at least 90% purity;

e. distilling the mother liquor of step (d) to isolate the residue containing monochlorodiphenyl sulfones and diphenyl sulfones;

f. optionally treating the residue of step (c) with liquor ammonia to give a mixture of diphenyl sulfone and 2-aminodiphenyl sulfone followed by acid treatment in the presence of alkanol and repeatedly extracting with halogenated solvent to obtain 2-aminodiphenyl sulfone further purified with aqueous alkanol; and g. optionally treating the residue of monochlorodiphenyl sulfone obtained in step (e) with liquor ammonia to give a 2-aminodiphenyl sulfone which is further purified with aqueous alkanol.

18. A process according to claim 17 wherein the solvent in step (a) is selected from alkanols such as methanol, ethanol, isopropanol, isobutanol; ethers such as 1,4-dioxane, methylcellosolve, ethylcellosolve; halogenated hydrocarbons such as, dichloromethane, 1,2-dichloroethane; aromatic hydrocarbons such as benzene, toluene, xylene, used in ratio of solvent to reaction mixture on weight basis is 1:1 to 1:10, preferably 1:2 to 1:6.

19. A process according to claim 17 wherein the dehalogenation reaction of isomeric mixture of dichlorodiphenyl sulfone is carried out in hydrogen in the presence of a reduction catalyst and dehydrohalogenating agent in a temperature range of 20 to 200° C., preferably 20 to 120° C. and at atmospheric pressure to 50 Bar, preferably atmospheric pressure to 15 Bar.

20. A process according to claim 17 wherein the reduction catalyst is selected from metal catalyst such as Raney Nickel, Palladium on carbon or Platinum on carbon, used in concentrations of 1 to 40% by weight on the basis of dichlorodiphenyl sulfone, preferably at 10 to 30%.

21. A process according to claim 17 wherein the dehydrohalogenating agent is selected from ammonia, triethyl amine, triethanol amine, with the ratio of dehydrohalogenating agent to the dichlorodiphenyl sulfone being in the range of 1:0.1-1:5 by weight, preferably is 1:0.5-1:3.

22. A process according to claim 17 wherein the solvent used for purification is selected from halogenated hydrocarbons such as dichloromethane, 1,2-dichloroethane; aromatic halogens, such as chlorobenzene, trichloroethylene and tetrachloroethylene the preferred solvents being 1,2-dichloroethane, and chlorobenzene, wherein the ratio of solvent to the crude diphenyl sulfone 1:1-1:10 by weight; preferably 1:2-1:5.

23. A process according to claim 17 wherein the oxidizing agent is selected from peroxides such as hydrogen peroxide, chlorates, peroxydisulfates or a mixture thereof.

24. A process according to claim 17 wherein the solvent used for separation and re-crystallization of diphenyl sulfone from monochloro diphenyl sulfones is selected from halogenated hydrocarbons like dichloromethane, 1,2-dichloroethane; aromatic halogens, such as chlorobenzene, trichloroethylene and tetrachloroethylene, the preferred solvents are 1,2-dichloroethane, and chlorobenzene.

25. A process according to claim 17 wherein the mixture of diphenyl sulfone and monochlorodiphenyl sulfones is ammonolysed with liquor ammonia at 100-300° C., preferably 200-250° in presence of a catalyst wherein, the ratio of mixture of diphenyl sulfone and monochlorodiphenyl sulfones to liquor ammonia on weight basis is 1:1-1:10, preferably 1:2-1:5.

26. A process according to claim 17 wherein the residue of step "e" containing residual 2-chlorodiphenyl sulfone is ammonolysed with liquor ammonia at 100-300° C., preferably at 200-250° in presence of a catalyst wherein the ratio of 2-chlorodiphenyl sulfone to liquor ammonia on weight basis is 1:1-1:10, preferably 1:2-1:5.

27. A process according to claim 17 wherein the catalyst is selected from metal chlorides or metal sulfates like copper chloride, cuprous chloride, and copper sulfate.

28. A process according to claim 1 further comprising conversion of residual isomeric mixture of dichlorodiphenyl sulfones to pure 2,4'-dihydroxydiphenyl sulfone and 4,4'-dihydroxydiphenyl sulfone in steps comprising:

(i). reacting isomeric mixture of dichlorodiphenyl sulfone with an aqueous solution of alkali in optionally aqueous or organic solvent or in mixture thereof, (ii). separating the unreacted dichlorodiphenyl sulfone by filtration, (iii). isolating crude mixture of 2,4'-dihydroxydiphenyl and 4,4'-dihydroxydiphenyl by precipitating with sulfuric or hydrochloric acid, (iv). dissolving the precipitating mixture in aqueous solution of sodium hydroxide, (v). separating of 4,4'-dihydroxydiphenysulfone, in form of monoalkali metal salt by adjusting the pH to 10.5-11.0 with sulfuric or hydrochloric acid, (vi). separating 2,4'-dihydroxydiphenyl sulfone from mother liquor of step (v), by adjusting pH to 5.0-5.5 with sulfuric or hydrochloric acid, and (vii). purifying crude 2,4'-dihydroxydiphenyl sulfone and 4,4'-dihydroxydiphenyl sulfone by crystallization in aqueous alkanol.

29. A process according to claim 28, the reaction is carried out at 100° C.-300° C., preferably 180-250° C., more preferably 200-240° C.

30. A process according to claim 28 wherein the alkali is selected from sodium hydroxide, potassium hydroxide, lithium hydroxide preferably sodium hydroxide, in the weight ratio of alkali:dichlorodiphenyl sulfone being 1:2-1:10, preferably 1:3-1:8.

31. A process according to claim 28 wherein the solvent is selected from water; alkanol such as methanol, ethanol, isopropanol, alkanol-water mixture or halogenated aliphatic solvents such as dichloromethane, 1,2-dichloroethane or halogenated aromatic solvents like chlorobenzene, o-dichlorobenzene.

32. A process according to claim 28 wherein the weight ratio of dichlorodiphenyl sulfone:water as solvent is 1:2-1:10, preferably 1:2-1:5.

33. A process according to claim 28 wherein the weight ratio of dichlorodiphenyl sulfone:organic solvent is 1:1.0-1:10 preferably 1:1.0-1:5.

34. A process according to claim 28 wherein the weight ratio of dichlorodiphenyl sulfone:organic solvent-water mixture is 1:2-1:10, preferably 1:2-1:5.

35. A process according to claim 28 wherein the weight ratio of organic solvent-water mixture containing solvent: water is 1:1 to 1:6, preferably 1:2-1:5.

36. A process according to claim 28 wherein the solvent for purification by crystallization aqueous alkanol wherein the akanol is selected from methanol, ethanol, isopropanol.

* * * * *